(12) United States Patent
Shute

(10) Patent No.: US 12,083,268 B2
(45) Date of Patent: *Sep. 10, 2024

(54) DELIVERY DEVICE AND FORMULATION

(71) Applicant: Ockham Biotech Limited, Fareham (GB)

(72) Inventor: Janis Kay Shute, Fareham (GB)

(73) Assignee: OCKHAM BIOTECH LIMITED, Fareham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,486

(22) Filed: Nov. 21, 2022

(65) Prior Publication Data

US 2023/0149643 A1 May 18, 2023

Related U.S. Application Data

(63) Continuation of application No. 16/315,051, filed as application No. PCT/GB2017/051959 on Jul. 3, 2017, now Pat. No. 11,541,192.

(30) Foreign Application Priority Data

Jul. 4, 2016 (GB) ..................................... 1611639

(51) Int. Cl.
| | | |
|---|---|---|
| A61M 15/00 | (2006.01) | |
| A61K 9/00 | (2006.01) | |
| A61K 31/137 | (2006.01) | |
| A61K 31/537 | (2006.01) | |
| A61K 31/573 | (2006.01) | |
| A61K 31/727 | (2006.01) | |
| A61K 45/06 | (2006.01) | |
| A61M 11/00 | (2006.01) | |
| A61P 11/00 | (2006.01) | |

(52) U.S. Cl.
CPC ....... *A61M 15/0085* (2013.01); *A61K 9/0078* (2013.01); *A61K 31/137* (2013.01); *A61K 31/573* (2013.01); *A61K 31/727* (2013.01); *A61K 45/06* (2013.01); *A61M 11/005* (2013.01); *A61P 11/00* (2018.01); *A61M 2209/06* (2013.01)

(58) Field of Classification Search
CPC ............. A61M 15/0085; A61K 9/0078; A61K 31/137; A61K 31/573; A61K 31/727; A61K 45/06; A61K 2300/00; A61P 11/00
See application file for complete search history.

(56) References Cited

U.S. PATENT DOCUMENTS

| | | | |
|---|---|---|---|
| 4,239,754 A | 12/1980 | Sache et al. | |
| 6,962,151 B1 | 11/2005 | Knoch et al. | |
| 11,541,192 B2 * | 1/2023 | Shute ............... | A61K 9/0078 |
| 2008/0175887 A1 * | 7/2008 | Wang ............... | A61K 31/436 |
| | | | 623/1.42 |
| 2015/0265582 A1 | 9/2015 | Armer et al. | |
| 2016/0175545 A1 | 6/2016 | Fink et al. | |
| 2018/0008540 A1 | 1/2018 | Narasimhan et al. | |

FOREIGN PATENT DOCUMENTS

| | | |
|---|---|---|
| EP | 1847256 A1 | 10/2007 |
| WO | 1994/010567 A1 | 5/1994 |
| WO | 2001/093846 A2 | 12/2001 |
| WO | 2003/068187 A1 | 8/2003 |
| WO | 2003/068188 A1 | 8/2003 |
| WO | 2003/068254 A1 | 8/2003 |
| WO | 2004073584 A2 | 9/2004 |
| WO | 2005/009323 A2 | 2/2005 |
| WO | 2005/025540 A2 | 3/2005 |
| WO | 2007/090646 A1 | 8/2007 |
| WO | 2012/073025 A1 | 6/2012 |

OTHER PUBLICATIONS

De Boer, A., et al., "Pulmonary," Chapter 6 in "Practical Pharmaceutics: An International Guideline for the Preparation, Care and Use of Medicinal Products," Bouwman-Boer, Y., et al., eds., Springer 2009, pp. 99-129.
International Search Report and Written Opinion dated Sep. 22, 2017 from International Application No. PCT/GB2017/051959 (Authorized Officer, K. Madalinska), 10 pages.
Carvalho et al., "The function and performance of aqueous aerosol devices for inhalation therapy", Journal of Pharmacy and Pharmacology, 2016, 23 pages.
Arzu Ari, "Jet, ultrasonic, and mesh nebulizers: an evaluation of nebulizers for better clinical outcomes", Eurasian J. Pulmonol., 2014, vol. 16, pp. 1-7.
M. Kunitz, "Crystalline desoxyribonuclease: I. Isolation and general properties spectrophotometric method for the measurement of desoxyribonucelase activity", J. Gen. Physiol., 1950, vol. 33, No. 4, pp. 349-362.
Ghazanfari et al., "The influence of fluid physiocochemical properties on vibrating-mesh nebulization", Int. J. Pharm., 2007, vol. 339, pp. 103-111.
Ehrlich et al., "Chemistry and pharmacology of heparin", J. Pharm. Sci., 1973, vol. 62, No. 4, pp. 517-545.
Guo et al., "Determination of molecular weight of heparin by size exclusion chromatography with universal calibration", Anal. Biochem., 2003 Vol. 312, pp. 33-39.

(Continued)

*Primary Examiner* — Mina Haghighatian
(74) *Attorney, Agent, or Firm* — MH2 TECHNOLOGY LAW GROUP, LLP

(57) ABSTRACT

The present invention relates to a handheld vibrating mesh nebuliser for delivery of a medicament to the respiratory system in therapy. The present invention also relates to a supply container for loading the nebuliser with liquid medicament. The present invention also relates to a kit for delivery of a medicament to a respiratory system and a method of loading a vibrating mesh nebuliser with liquid medicament from a supply container. The present invention also relates to compositions for use in a method of treatment of a respiratory disease in a patient by therapy.

20 Claims, 11 Drawing Sheets

(56) References Cited

OTHER PUBLICATIONS

Bendstrup et al., "Characterization of heparin aerosols generated in jet and ultrasonic nebulisers", J. Aerosol Med., 1999, vol. 12, No. 1, pp. 17-25.
Lenney et al., "Lung deposition of inhaled tobramycin with eFlow rapid/LC Plus jet nebuliser in healthy and cystic fibrosis subjects", J. Cyst. Fibros., 2011, vol. 10, pp. 9-14.
M. Kunitz, "Crystalline desoxyribonuclease: Digestion of thymus nucleic acid (desoxyribonucleic acid) the kinetics of the reaction", J. Gen. Physiol., 1950, vol. 33, No. 4, pp. 363-377.
Quanjer et al., "Lung volumes and forced ventilatory flows", European Resp. Journal, 1993, vol. 6, Suppl. 16, pp. 5-40.
N. B. Kurnick, "The Determination of Desoxyribonuclease Activity by Methyl Green; Application to Serum" Arch. Biochem., 1950, vol. 29, pp. 41-54.
Paul A. Janmey, "A torsion pendulum for measurement of the viscoelasticity of biopolymers and its application to actin networks", J. Biochem. Biophys. Methods, 1991, vol. 22, No. 1, pp. 41-53.
Labarca et al., "A simple, rapid, and sensitive DNA assay procedure", Anal. Biochem., 1980, vol. 102, No. 2, pp. 344-352.
Boe et al., "European Respiratory Society Guidelines on the use of Nebulizers", Eur. Respir. J., 2001, vol. 18, pp. 228-242.
Liberti et al., "Physicochemical Studies of Fractionated Bovine Heparin: II. Viscosity as a Function of Ionic Strength", Archives of Biochemistry and Biophysics, 1967, vol. 119, pp. 510-518.
Dixon et al., "Nebulized heparin is associated with fewer days of mechanical ventilation in critically ill patients: a randomized controlled trial", Critical Care, 2010, vol. 14, No. 5, p. R180, 10 pages.
Anonymous, "Inhalation", Apr. 2016, XP055404040, Retrieved from the Internet: URL:https://web.archive.org/web/20160401203531/http://www.mtj.de/index.php/inhalation, 11 pages.
Anonymous, "Aeroneb Pro—Micropump Nebulizer", 2004, XP055404051, Retrieved from the Internet: https://www.tri-anim.com/data/default/productattachments/THS-Aerogen-Aeroneb-Pro.pdf, 2 pages.
Glas et al., "Hepburn—investigating the efficacy and safety of nebulized heparin versus placebo in burn patients with inhalation trauma: study protocol for a multi-center randomized controlled trial", Trials, 2014, vol. 15, No. 91, pp. 1-11.
Hibbitts et al., "Investigation of Fluid Physicochemical Properties on Output in Vibrating Mesh Nebulisers", ISAM poster, 200 RCSI, St. Stephen's Green, 2010, 1 page.
Beck-Broichsitter et al., "Boosting the aerodynamic properties of vibrating-mesh nebulized polymeric nanosuspensions", International Journal of Pharmaceutics, 2014, vol. 459, pp. 23-29.
Charm et al., "Shear Inactivation of Heparin", Biorheology, 1975, vol. 12, p. 93.
Robert M. DiBlasi, "Clearing the Mist from Our Eyes: Bronchodilators, Mechanical Ventilation, New Devices, Locations, and What you should know about Bias Flow", Respiratory Care, 2010, vol. 55, No. 7, pp. 942-946.
Jaspe et al., "Do Protein Molecules unfold in a Simple Shear Flow?", Biophysical Journal, 2006, vol. 91, pp. 3415-3424.
Tuinman et al., "Nebulized anticoagulants for acute lung injury—a systematic review of preclinical and clinical investigations", Critical Care, 2012, vol. 16, No. R70, 10 pages.
Charm et al., "Shear Degradation of heparin", Biorheology, 1975, vol. 12, p. 275-278.
Lentz et al., "Rationale for the Selection of an Aerosol Delivery System for Gene Delivery", Journal of Aerosol Medicine, 2006, vol. 19, No. 3, pp. 372-384.
Marszalek et al., "The Force-Driven Conformations of Heparin Studied with Single Molecule Force Microscopy", Biophysical Journal, 2003, vol. 85, pp. 2696-2704.
Persson et al., "The Effects of Food on the Dissolution of Poorly Soluble Drugs in Human and in Model Small Intestinal Fluids", Pharmaceutical Research, 2005, vol. 22, No. 12, pp. 2141-2151.
Waldrep et al., "Advanced Nebulizer Designs Employing Vibrating Mesh/Aperture Plate Technologies for Aerosol Generation", Current Drug Delivery, 2008, vol. 5, pp. 114-119.
L.B. Jaques, "Heparins—Anionic Polyelectrolyte Drugs", Pharmacological Reviews, 1980, vol. 31, No. 2, 68 pages.
Ari et al., "Influence of Nebulizer Type, Position, and Bias Flow on Aerosol Drug Delivery in Simulated Pediatric and Adult Lung Models During Mechanical Ventilation", Respiratory Care, 2010, vol. 55, No. 7, pp. 845-851.
Stivala et al., "Physicochemical Studies of Fractionated Bovine Heparin, III. Some Physical Parameters in Relation to Biological Activity", Archives of Biochemistry and Biophysics, 1967, vol. 122, pp. 32-39.
Lee et al., "Nano spray drying: A novel method for preparing protein nanoparticles for protein therapy", International Journal of Pharmaceutics, 2011, vol. 403, pp. 192-200.
Dixon et al., "A phase 1 trial of nebulised heparin in acute lung injury", Critical Care, 2008, vol. 12, No. 3, R64, 8 pages.
Simmons et al., "In vitro comparison of an electronic micro pump nebulizer with other high efficiency nebulizers", Abstract, Journal of Allergy and Clinical Immunology, 2004, vol. 113, Issue 2, p. S32.
Beck-Broichsitter et al., "Controlling the droplet size of formulations nebulized by vibrating-membrane technology", European Journal of Pharmaceutics and Biopharmaceutics, 2014, vol. 87, pp. 524-529.
Zhang et al., "Performance of the Vibrating Membrane Aerosol Generation Device: Aeroneb Micropump Nebulizer™", Journal of Aerosol Medicine, 2007, vol. 20, No. 4, pp. 408-416.
Glas et al., "Nebulized heparin for patients under mechanical ventilation: an individual patient data meta-analysis", Annals of Intensive Care, 2016, vol. 6, No. 33, 8 pages.
Rajiv Dhand, "Nebulizers That Use a Vibrating Mesh or Plate with Multiple Apertures to Generate Aerosol", Respiratory Care, 2002, vol. 47, No. 12, pp. 1406-1418.
Joseph L Rau, "Design Principles of Liquid Nebulization Devices Currently in Use", Respiratory Care, 2002, vol. 47, No. 11, pp. 1257-1278.
Pfizer Ltd., "Heparin Injection, heparin sodium injection (porcine mucous)", Product Information, Heparin CAS Registry Number is 9005-19-6, Oct. 6, 2012, 13 pages.
Porter et al., "The Entanglement Concept in Polymer systems", Chemical Reviews, 1966, vol. 66, No. 1, pp. 1-27.
Kendrick et al., "Selecting and using nebuliser equipment", Thorax, 1997, vol. 52, Suppl. 2, pp. S92-S101.
Holt et al., "Use on inhaled heparin/N-acetylcysteine in inhalation injury: does it help?" Abstract, J. Burn Care Res., 2008, vol. 29, No. 1, pp. 192-195.
Trowbridge et al., "Dermatan sulfate: new functions from an old glycosaminoglycan", Glycobiology, 2002, vol. 12, No. 9, pp. 117R-125R.
V. V. Kakkar, "Low-dose heparin to low molecular weight heparin prophylaxis: in pursuit of excellence—a person perspective", Journal of Thrombosis and Haemostasis, 2005, vol. 3, pp. 195-209.
J. E. Coates, "Lung Function: Assessment and Applications in Medicine", 4th Edition, Oxford, Blackwell Scientific Publications, 1969, Chapter 14, pp. 328-387.
Sinicropi et al., "Colorimetric determination of DNase I activity with a DNA-methyl green substrate", Analytical Biochemistry, 1994, vol. 222, No. 2, pp. 351-358.
Sagent Pharmaceuticals, Inc., "Heparin Sodium Injection, USP", Material Safety Data Sheet, Feb. 9, 2009, pp. 1-8.
Sagent Pharmaceuticals, "Heparin Sodium—Heparin Sodium Injection, Solution", Prescribing Information, revised Jun. 2017, 24 pages.
"Heparin—Wikipedia, the free encyclopedia", https://en.wikipedia.org/w/index.php?title=Heparin&oldid=724018004, archived page dated Jun. 6, 2016, 18 pages.
Office Action dated Jun. 24, 2024 for corresponding European Application No. 17736753.9, 6 pages.

* cited by examiner

DELIVERY DEVICE AND FORMULATION

CROSS-REFERENCE TO RELATED APPLICATION

This application is a continuation of U.S. patent application Ser. No. 16/315,051 filed 3 Jan. 2019, which is a U.S. National Stage application of PCT/GB2017/051959 filed 3 Jul. 2017, which claims priority to Great Britain Application No. 1611639.4 filed 4 Jul. 2016, the contents of which are incorporated herein by reference in their entirety.

FIELD OF THE INVENTION

The present invention relates to a handheld vibrating mesh nebuliser for delivery of a medicament to the respiratory system in therapy. The present invention also relates to a supply container for loading the nebuliser with liquid medicament. The present invention also relates to a kit for delivery of a medicament to a respiratory system and a method of loading a vibrating mesh nebuliser with liquid medicament from a supply container. The present invention also relates to compositions for use in a method of treatment of a respiratory disease in a patient by therapy.

BACKGROUND INFORMATION

Vibrating mesh nebulisers can be classified as micropump systems because aerosol generation from this technology is usually a result of energy forcing liquid to flow through small apertures of a plate or membrane. There are two main types of micropump nebulisers: passive or active vibrating mesh systems. The passive vibrating mesh nebuliser (e.g. Omron MicroAir; Omron Healthcare, Inc., Lake Forest, IL) is composed of a piezoelectric crystal which generates vibration from electrical force to a transducer horn that is in contact with the liquid formulation. The vibration then creates waves in the nebuliser reservoir that travel towards a perforated plate positioned in front of the transducer horn. Consequently, aerosol droplets are created once the fluid flowing through the membrane is enough to cause drop detachment [1,2].

In contrast, active vibrating mesh nebulisers (e.g. Aerogen Aeroneb® [Aerogen, Inc., Galway, Ireland] and PARI eFlow® [PARI Respiratory Equipment, Inc., Midlothian, VA]) have a dome-shaped membrane (aperture sizes of approximately 4 µm and 2-20 µm, respectively [3]) directly connected to a vibrating piezoelectric element. Following application of electric current, said membrane starts to vibrate at high frequency (over 100,000 times per second), and the liquid formulation is rapidly extruded through the mesh as a consequence of the downward and upward movements of the membrane; this action generates the aerosol droplets [1]. The vibrating mesh nebuliser creates a fine particle, low velocity aerosol optimized for targeted delivery through the lungs. It is designed to produce an aerosol from a drug in liquid format without damaging or altering the molecular integrity or the concentration of the compound.

Both active and passive vibrating mesh nebulisers may be highly dependent on formulation characteristics. The influence of bulk liquid characteristics on aerosol generation of solutions has been systematically evaluated. Both systems have been demonstrated to ineffectively produce aerosols from solutions that have high viscosities [4]. The passive mesh technology yields slightly larger droplets than the active mesh system, but compensates to provide a similar respirable output by having a higher total aerosol output. An increased viscosity provides a decrease in droplet size, and a consequently higher respirable output from both mesh systems, but the overall output rate is compromised for passive mesh nebulisers. The influence of surface tension on aerosol properties is less clear, but it is known that fluids with low viscosity and low surface tension seem more desirable for greater nebulisation performance. With the PARI eFlow® nebuliser, an increase in solution viscosity led to a decrease both in aerodynamic diameter and output rate, whilst an increase in the electrolyte concentration led to an increase in output rate and a decrease in aerodynamic diameter. Therefore, the proportion of respirable droplets generated is dependent on the interplay between output rate and aerodynamic diameter, which in turn are each highly driven by the physicochemical properties of the formulation [1,2].

A low ion concentration is crucial for providing less variable aerosol generation with vibrating-mesh nebulisers. Investigations using several sodium halides showed that solutions containing ions with greater polarizing abilities (i.e. NaI) presented superior aerosol performance due to their greater presence at the air-water interface [1]. In general, active vibrating mesh nebulisers deliver solutions of low viscosity more efficiently than jet nebulisers, while passive devices present comparable performance [1]. Overall, mesh nebulisers are not compatible with viscous liquids or those that crystallise on drying [2 (Table 1),4]. The Omron (passive) and Aeroneb® Pro (active) vibrating mesh nebulisers were both shown to be unsuitable for delivery of highly viscous liquids, since nebulisation was intermittent or ceased completely [4].

Glycosaminoglycans, such as heparin, are known to be effective in the treatment of several respiratory diseases, such as chronic obstructive pulmonary disease (COPD) [5]. Heparin is a polydisperse high molecular weight polysaccharide [6]. It behaves as a typical polyelectrolyte in aqueous solution due to its high negative charge. Therefore physicochemical measurements, including measurements of intrinsic viscosity, are sensitive to pH and ionic strength. Heparin forms highly viscous solutions in water, but there is a decrease in intrinsic viscosity with increasing ionic strength [6]. Adding cations shields the negative charges on heparin and reduces the extended coil conformation, reducing the hydrodynamic radius and thus the intrinsic viscosity [7].

Bendstrup et al. reported that the kinematic viscosity (dynamic viscosity/density) of heparin solutions increased with increasing concentration, and with decreasing temperature [8]. Calcium heparin had a lower viscosity than sodium heparin, and output (IU/min) from an ultrasonic nebuliser was maximum at 7000 IU/ml and a kinematic viscosity of 3 cSt (3 centistokes). Output was reduced at higher concentrations and viscosities. Surface tension has little effect on aerosolisation properties of heparin. The intrinsic viscosity of heparin (average molecular weight 13.5-15 kDa) in water is much higher (80.6 mL/g) than other polymers of similar or even greater size such as Ficoll F-30 (6.8 mL/g, molecular weight 21,292) and pullulan P-20 (18.1 mL/g, molecular weight 22,800), which are both non-ionic polymers [7].

Therefore, it has not been thought possible that glycosaminoglycan solutions, such as heparin solutions, could be delivered from vibrating mesh nebulisers, and particularly not in a volume and at a concentration that will be useful in the treatment of COPD and other pulmonary diseases, if they are delivered at all.

SUMMARY OF THE INVENTION

The present invention is based on the unexpected finding that it is possible to nebulise a liquid formulation containing a polymeric material, such as a glycosaminoglycan with a molecular weight>8 kDa, using a vibrating mesh nebuliser. Hence, notwithstanding their viscosity, the invention provides for the first time the possibility of using such nebulisers with polymeric materials in treating respiratory disorders.

In one aspect, the present invention provides a vibrating mesh nebuliser to deliver a medicament to a respiratory system, said nebuliser comprising:
  a housing having a reservoir for a liquid medicament; and
  a liquid medicament,
wherein the liquid medicament comprises a glycosaminoglycan or a physiologically acceptable salt thereof, and wherein the nebuliser is a handheld device.

In another aspect, the present invention provides a supply container for delivering a liquid medicament to a vibrating mesh nebuliser according to the invention, wherein the supply container comprises a liquid medicament as defined in the claims.

In another aspect, the present invention provides a kit for delivery of a medicament to a respiratory system, the kit comprising:
  (a) a vibrating mesh nebuliser, wherein the vibrating mesh nebuliser is a vibrating mesh nebuliser according to the invention or a vibrating mesh nebuliser that is not loaded with liquid medicament; and
  (b) one or more liquid medicament supply container(s) according to the invention.

In another aspect, the present invention provides a method of loading a vibrating mesh nebuliser with liquid medicament from a supply container according to the invention, wherein the method involves inserting said supply container into a vibrating mesh nebuliser which is not loaded with a liquid medicament, or wherein the method involves dispensing the liquid medicament from said supply container into a vibrating mesh nebuliser which is not loaded with a liquid medicament.

In another aspect, the present invention provides a composition for use in a method of treatment of a disease in a patient by therapy, in which method (i) the patient is treated by administering the composition to the respiratory system, and (ii) the composition is delivered to the respiratory system by a vibrating mesh nebuliser according to the invention, wherein the composition comprises a compound which is a glycosaminoglycan or a physiologically acceptable salt thereof, optionally wherein the compound is selected from the group consisting of heparin, unfractionated heparin, the sodium salt of heparin, heparin sulfate, and a derivative of any thereof.

DETAILED DESCRIPTION

Figure 1:
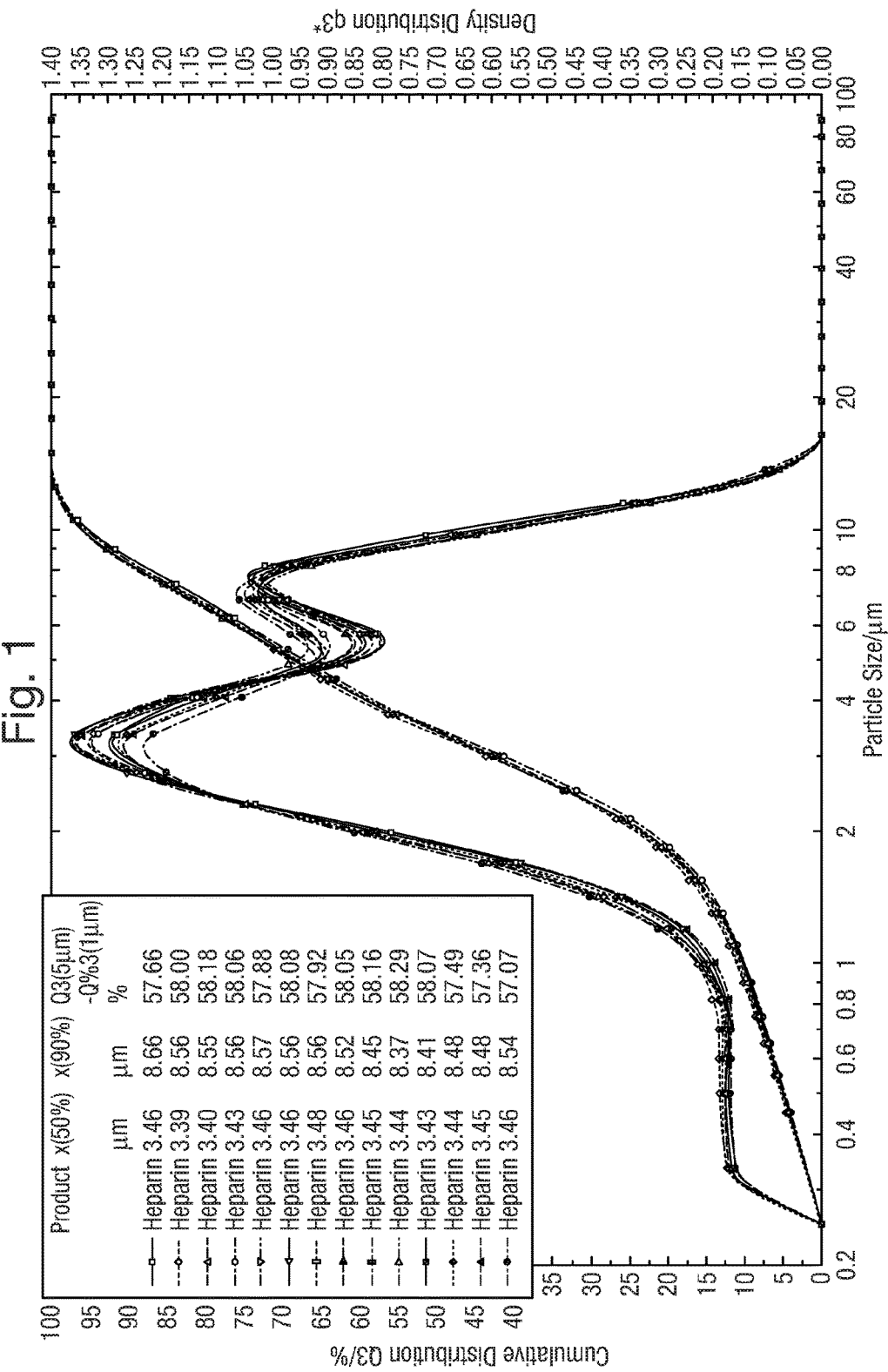
FIG. 1: Frequency density distribution and cumulative frequency distribution of particle size observed when aqueous solutions containing 31.25 mg/mL heparin and 154 mM NaCl are nebulised in the Aeroneb® Go.
Figure 2:
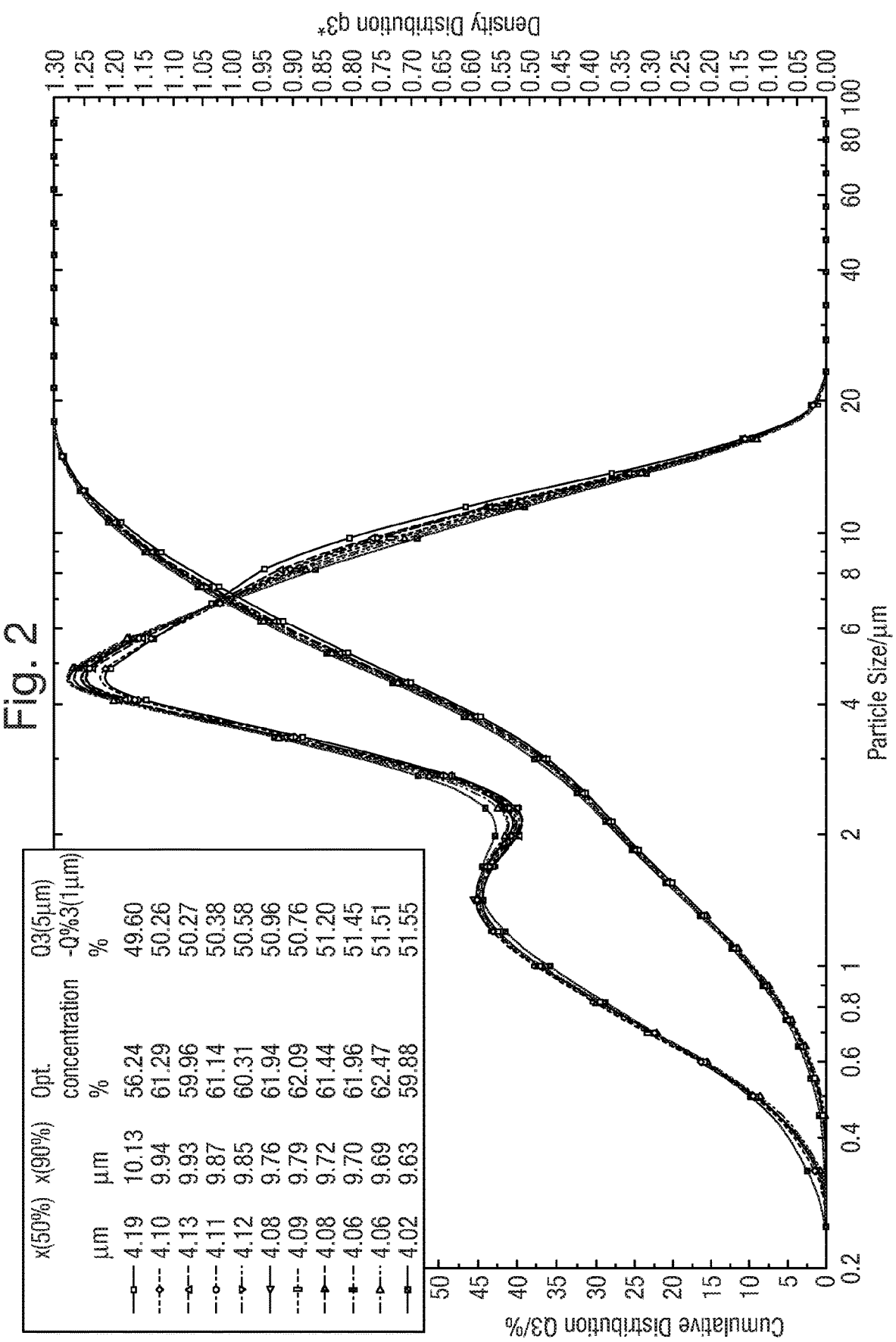
FIG. 2: Frequency density distribution and cumulative frequency distribution of particle size observed when aqueous solutions containing 40 mg/mL heparin and 140 mM NaCl are nebulised in the Aeroneb® Go.
Figure 3:
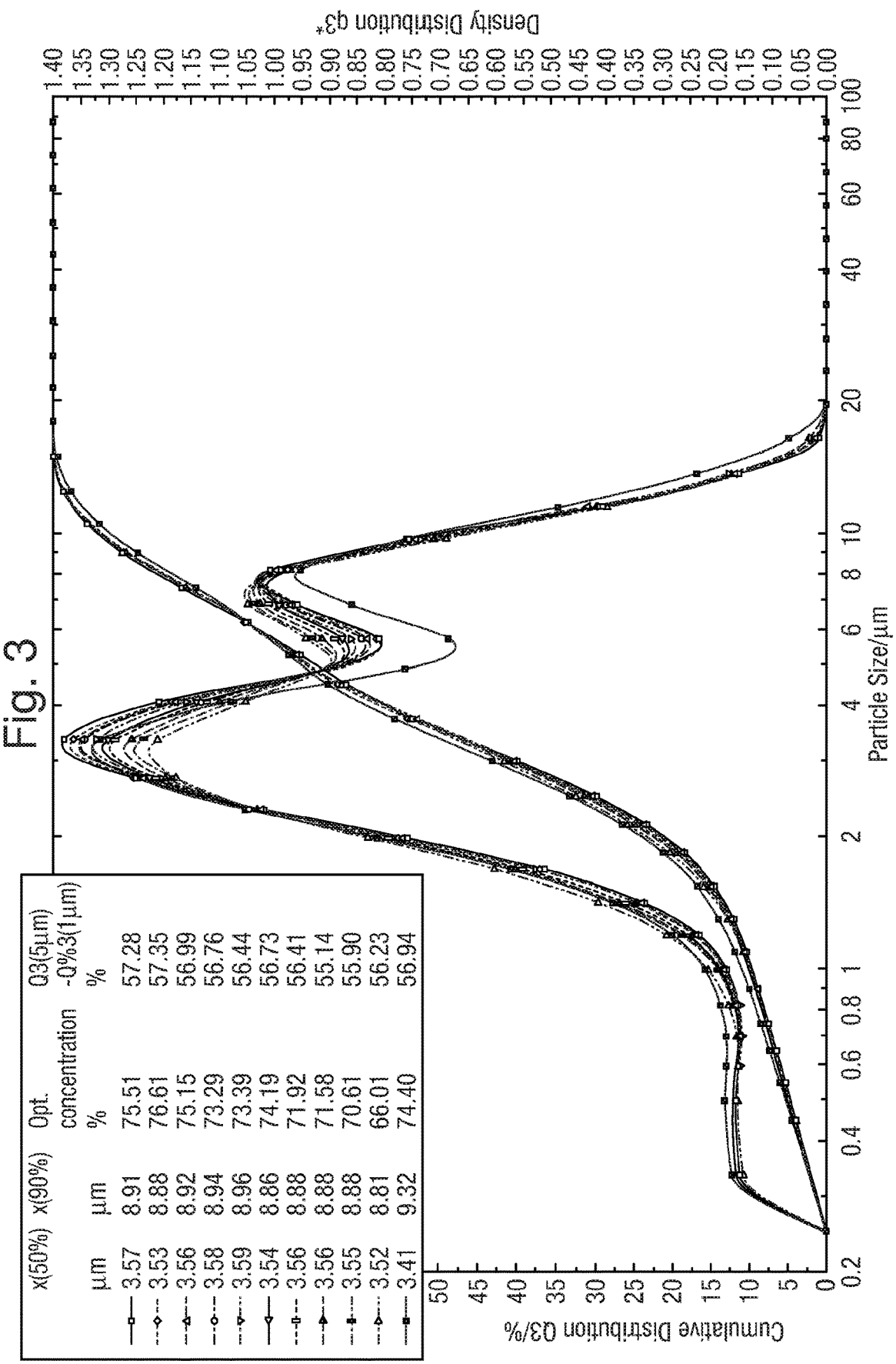
FIG. 3: Frequency density distribution and cumulative frequency distribution of particle size observed when aqueous solutions containing 40 mg/mL heparin and 168 mM NaCl are nebulised in the Aeroneb® Go.
Figure 4:
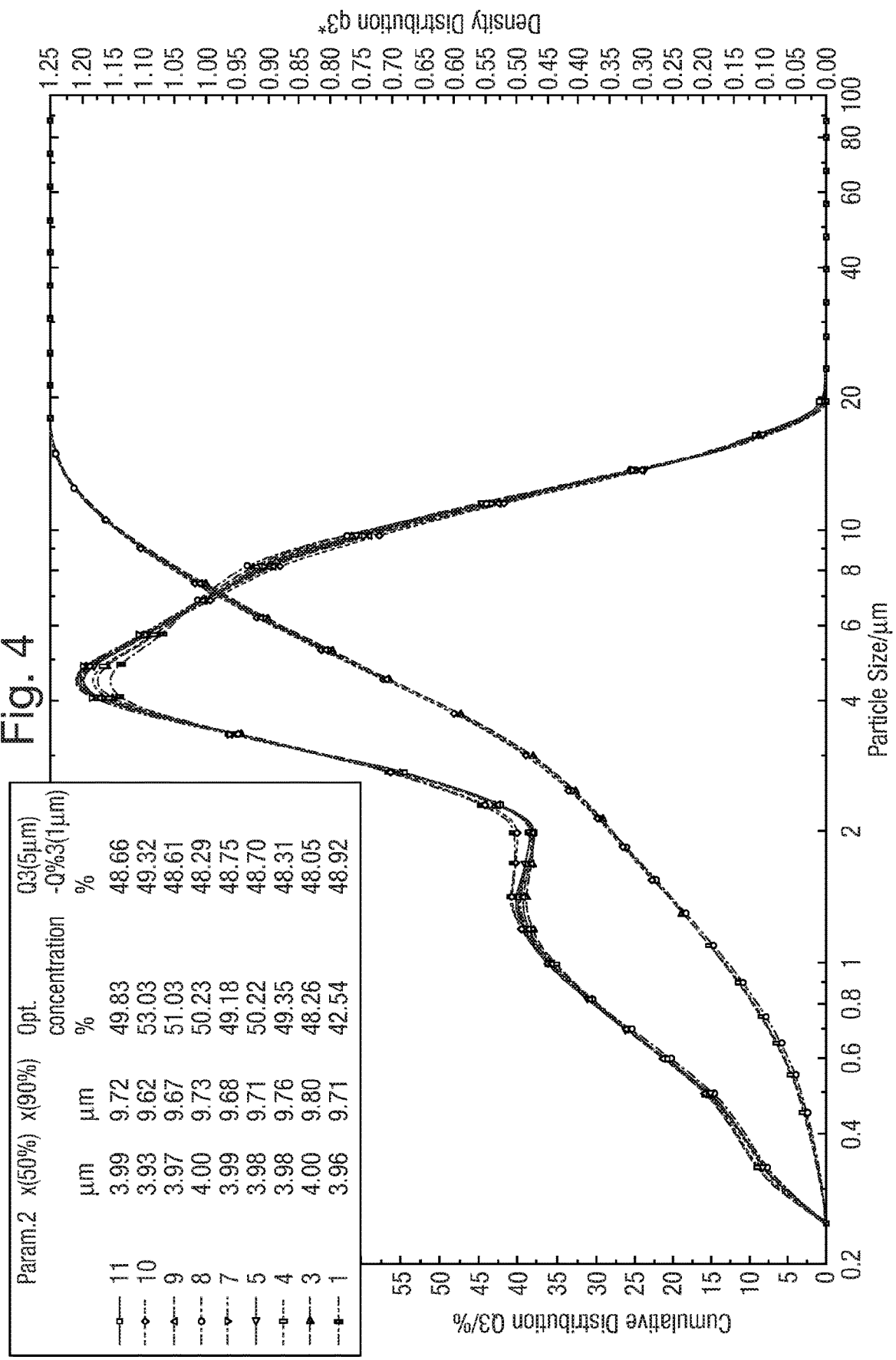
FIG. 4: Frequency density distribution and cumulative frequency distribution of particle size observed when aqueous solutions containing 40 mg/mL heparin and 196 mM NaCl are nebulised in the Aeroneb® Go.
Figure 5:
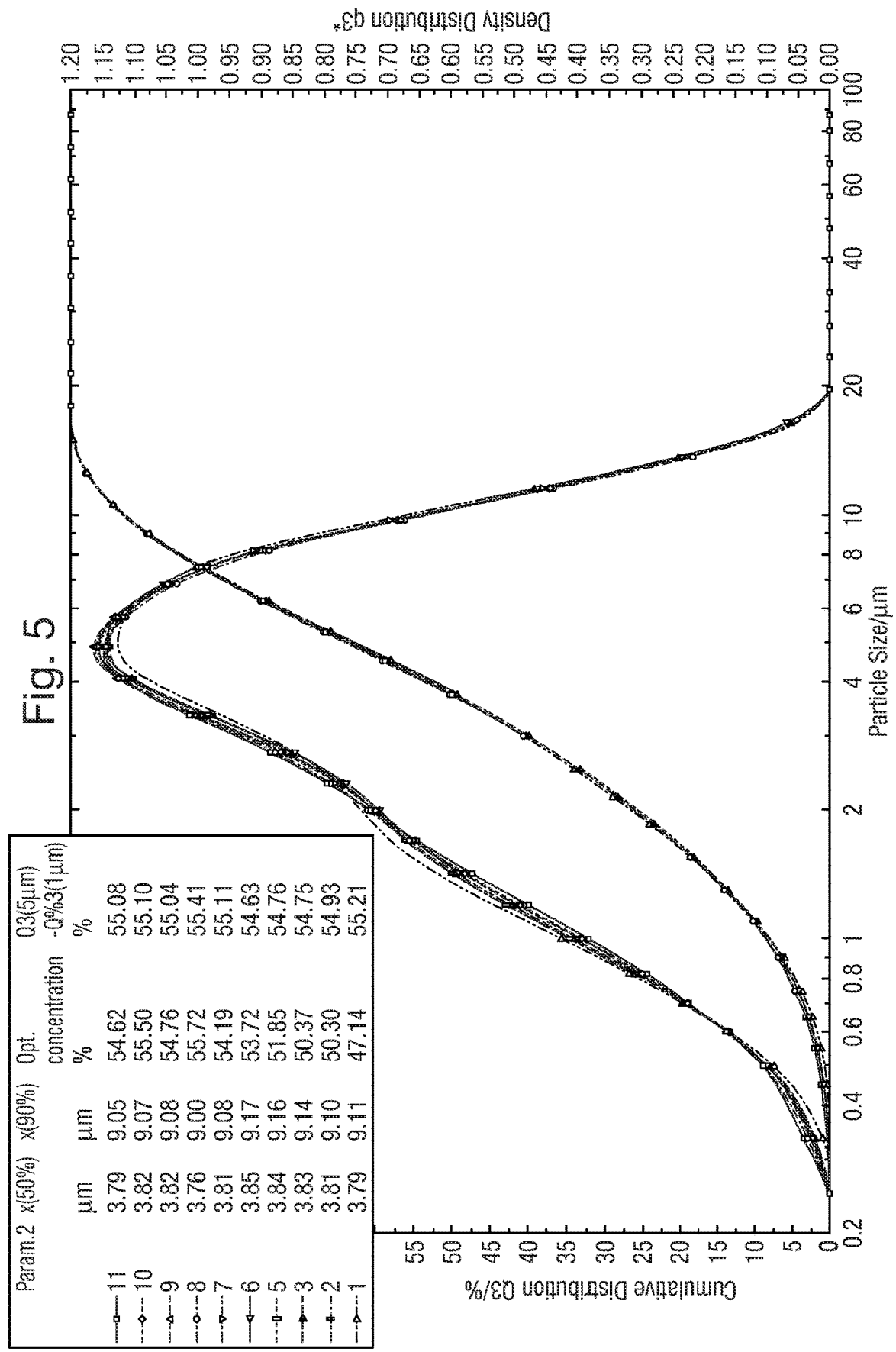
FIG. 5: Frequency density distribution and cumulative frequency distribution of particle size observed when aqueous solutions containing 40 mg/mL heparin and 210 mM NaCl are nebulised in the Aeroneb® Go.
Figure 6:
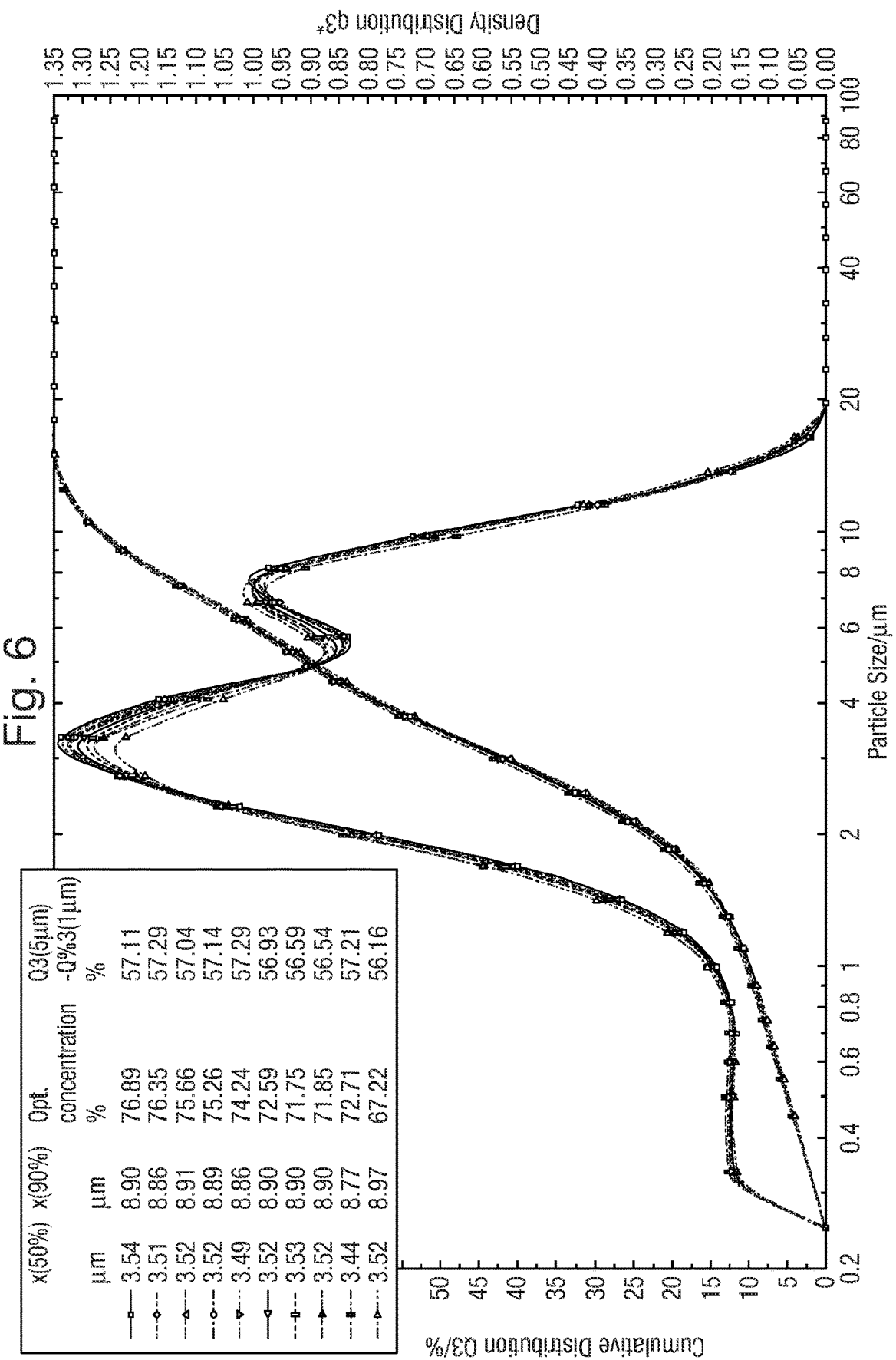
FIG. 6: Frequency density distribution and cumulative frequency distribution of particle size observed when aqueous solutions containing 40 mg/mL heparin and 224 mM NaCl are nebulised in the Aeroneb® Go.
Figure 7:
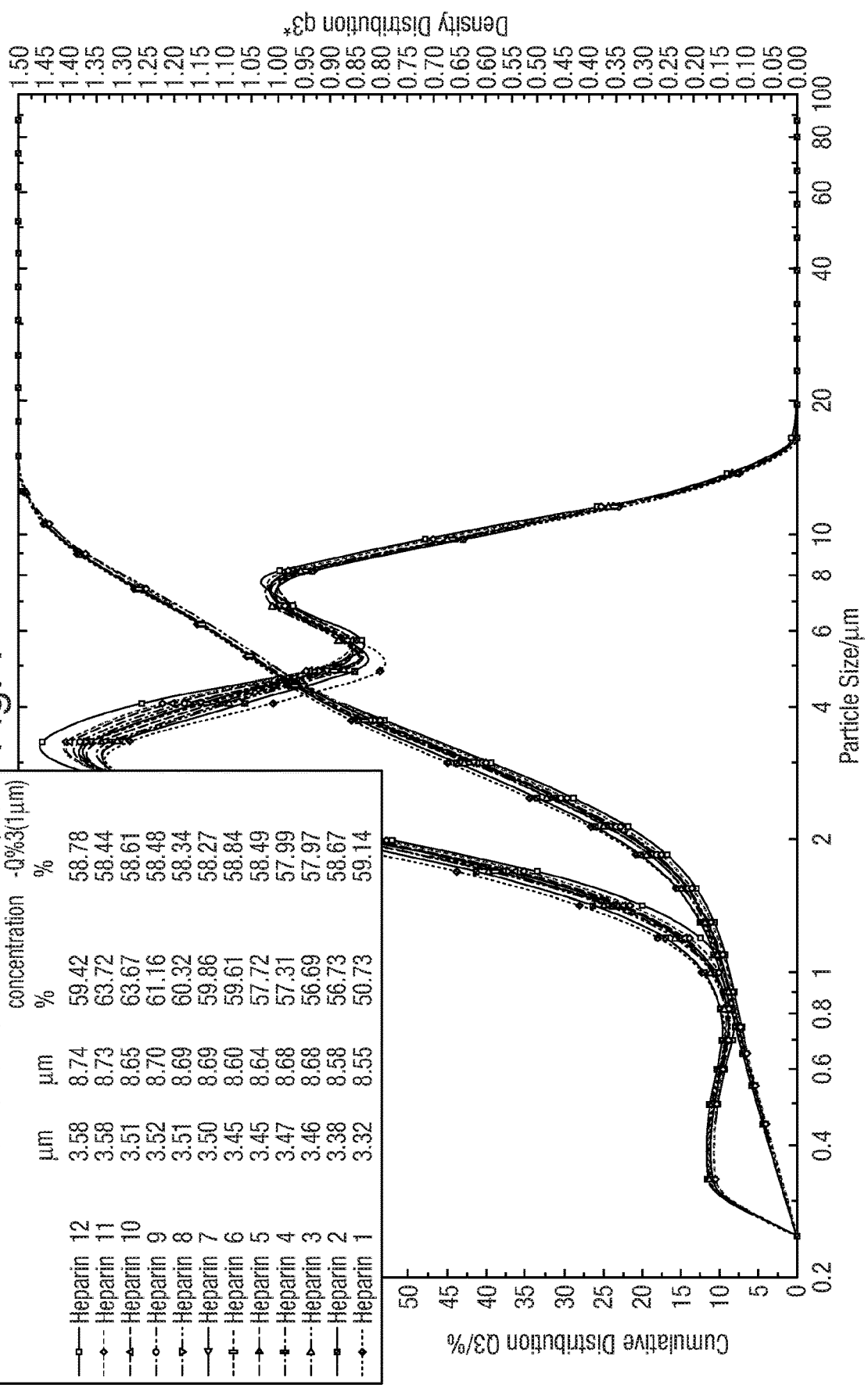
FIG. 7: Frequency density distribution and cumulative frequency distribution of particle size observed when aqueous solutions containing 40 mg/mL heparin, 112 mM NaCl and 56 mM $MgCl_2$ are nebulised in the Aeroneb® Go.

Herein, any reference to a term in the singular also encompasses its plural. Where the term "comprising", "comprise" or "comprises" is used in a particular embodiment, also encompassed are the embodiments wherein said term is substituted for "consisting of", "consist of" or "consists of" respectively, as well as embodiments where the term "comprising", "comprise" or "comprises" is substituted for "consisting essentially of", "consist essentially of" or "consists essentially of" respectively. Any reference to a numerical range or single numerical value also includes values that are about that range or single value. Any reference to a glycosaminoglycan also encompasses a physiologically acceptable salt thereof. Any reference to heparin, a heparin, or unfractionated heparin also encompasses a physiologically acceptable salt thereof.

The present invention is concerned with the administration of a liquid medicament comprising a glycosaminoglycan or a physiologically acceptable salt thereof to the respiratory system of a patient in need thereof. The glycosaminoglycan is typically delivered to the patient via a vibrating mesh nebuliser. The present invention is useful in particular in the treatment of respiratory disease and relief of symptoms of respiratory disease in a patient. Alternative and preferred features of the invention are described below, although are not intended to limit the scope of the invention. For the avoidance of doubt, all alternative and preferred features relating to the use of a glycosaminoglycan or physiologically acceptable salt thereof, or any other component such as a therapeutic agent or a DNase, in a liquid medicament apply equally to the use of said glycosaminoglycan or physiologically acceptable salt thereof, or said other component such as a therapeutic agent or a DNase, in a method of treatment of disease in a patient by therapy.

Vibrating Mesh Nebuliser

Nebulisers suitable for use in the present invention include any handheld nebuliser capable of nebulising a solution by the active process of vibrating mesh nebulisation. Such nebulisers include, but are not limited to, the vibrating mesh nebulisers described in, e.g., WO 2005/009323, the contents of which are herein incorporated by reference. The invention provides a handheld vibrating mesh nebuliser loaded with a medicament as defined herein.

In one embodiment, the present invention provides a vibrating mesh nebuliser to deliver a medicament to a respiratory system, said nebuliser comprising:
  a housing having a reservoir for a liquid medicament; and
  a liquid medicament,
wherein the liquid medicament comprises a glycosaminoglycan or a physiologically acceptable salt thereof,
and wherein the nebuliser is a handheld device.

In certain embodiments of the present invention, the reservoir of the vibrating mesh nebuliser has a liquid medicament inlet port and a medicament outlet port, and the vibrating mesh nebuliser may also further comprise:
  an aerosol generator comprising a vibratable membrane having a plurality of apertures extending between a first surface and a second surface thereof, in particular those as described in U.S. Pat. Nos. 5,164,740, 5,586,550, 5,758,637 and 6,085,740 (the contents of which are herein incorporated by reference), wherein the aerosol generator aerosolises at least a portion of the medicament into an aerosol;
  a gas venting inlet to permit a gas, preferably comprising air, to enter the nebuliser and form a mixture with the aerosol, wherein the gas venting inlet may or may not be located in close proximity to the aerosol generator;
  a passage through which the mixture of the aerosol and the gas is delivered to an outlet port of the nebuliser; or
  a combination thereof.

In certain embodiments, the aerosol generator may have a protector to protect the aerosol generator against physical damage. This protector may comprise an upper protector above the aerosol generator, or a lower protector below the aerosol generator, or a combination thereof. The protector may or may not comprise a mesh. The protector may or may not be integral with the nebuliser housing.

In one embodiment, the liquid medicament may be supplied from the reservoir to the aerosol generator by gravitational flow.

The vibrating mesh nebuliser according to the invention may optionally also comprise any or all, for instance, any one, two, three, four, five or all of the following features:
  a baffle to direct the mixture of the gas and the aerosol to the outlet port, wherein said baffle may optionally be inclined towards the outlet port, or may optionally further comprise an inclined surface oriented to cause aerosol flow through the outlet port;
  an aerosol rainout trap, which may or may not be adjacent to the outlet port;
  an aerosol generator housing in which the aerosol generator is held, optionally wherein the aerosol generator housing is fixed to the reservoir;
  a drive circuit for the aerosol generator;
  an electrical connector for supplying electrical power to the aerosol generator; and
  a respiratory connector to connect the outlet port to a respiratory system, optionally wherein the respiratory connector is selected from the group consisting of a mouthpiece, a face mask, and a nasal piece.

Particular examples of vibrating mesh nebulisers suitable for use in the present invention include, but are not limited to, the eFlow® device (PARI, Starnberg, Germany), handheld products in the Aeroneb® range (Aerogen Inc., Galway, Ireland), and handheld products in the InnoSpire range (Philips Respironics, Chichester, UK).

eFlow® (PARI, Starnberg, Germany): The PARI eFlow® is a battery-operated, compact, portable nebuliser using the ODEM TouchSpray atomising head that consists of a membrane with 4,000 laser-drilled apertures surrounded by a piezoelectric actuator to generate aerosol. Recent studies showed that the eFlow® can improve patient compliance due to short nebulization time [9]. Nebulization with the eFlow® is highly efficient at approximately 90% of the charge dose, with aerosol output at rates up to 1 mL/min, which leads to a short treatment duration [2].

Aerogen Aeroneb® (Aerogen, Inc., Galway, Ireland): The Aeroneb® Go (Philips Respironics) is a small lightweight device, designed for ambulatory patients and for use in the home. There are also several devices in the Aeroneb® range which are not handheld. For example, the Aeroneb® Solo is used for aerosol delivery via invasive and non-invasive ventilation, and the Aeroneb® NIVO is used for aerosol delivery during non-invasive ventilation. While the Aeroneb® Solo and NIVO provide an airtight seal in the ventilator circuit as an in-line device, their controller units limit their portability, unlike the Aeroneb® Go [2]. The Aeroneb® Pro is used for patients requiring positive pressure breathing assistance, including mechanical ventilation and delivery through an endotracheal tube. These devices are therefore designed for hospital use in non-ambulatory patients.

InnoSpire (Philips Respironics, Chichester, UK): The InnoSpire Go is a general purpose portable mesh device for COPD and Asthma patients. It is designed to reduce the total treatment burden by creating an easier user experience for the patient [10].

Any of the handheld devices mentioned herein may be employed in the invention. Any functionally equivalent device to those specific devices mentioned herein may be employed in the invention.

Hence, in any of the embodiments described herein, unless otherwise stated, the nebuliser is a handheld device. Handheld devices may be powered by a battery. In some embodiments, the vibrating mesh nebuliser has a fill volume of from 1 to 10 mL. Typically, a handheld vibrating mesh nebuliser may therefore be considered to be a vibrating mesh nebuliser with a fill volume of from 1 to 10 mL. Examples of handheld devices include, but are by no means limited to, the PARI eFlow®, the Aeroneb® Go and the InnoSpire Go. Such nebulisers are designed for ambulatory patients or patients who do not require assistance with breathing, and such patients represent one preferred patient group of the invention. These nebulisers are designed for use outside of hospitals or clinics, such as in the home, in the workplace or outside. In contrast, devices such as the Aeroneb® Pro are larger devices that are designed for use in hospitals by patients requiring assistance with breathing.

As outlined herein, in an especially preferred embodiment of the invention the device is a handheld device. However in an alternative embodiment, the device may not be limited to being handheld, but have the other features outlined herein. Thus, in one alternative embodiment, the present invention provides a vibrating mesh nebuliser to deliver a medicament to a respiratory system, said nebuliser comprising:

a housing having a reservoir for a liquid medicament; and
a liquid medicament, wherein the liquid medicament comprises a glycosaminoglycan or a physiologically acceptable salt thereof.

The vibratable membrane of the aerosol generator may vibrate at a single vibration frequency during the aerosolisation process, or the frequency at which it vibrates during the aerosolisation process may switch between two or more values. In the most preferred embodiment, the vibratable membrane of the aerosol generator vibrates at a single vibration frequency during the aerosolisation process.

During the aerosolisation process, heat may or may not be applied to the liquid medicament in the reservoir. In the most preferred embodiment, heat is not applied to the liquid medicament in the reservoir during the aerosolisation process.

Liquid Medicament

The vibrating mesh nebuliser of the present invention typically comprises a liquid medicament, which comprises a glycosaminoglycan or a physiologically acceptable salt thereof. In preferred embodiments, the glycosaminoglycan or salt thereof is useful in the treatment of respiratory disease, such as COPD. Hence, in an especially preferred embodiment the disease to be treated is COPD and in one such instance the sole, or main, therapeutic present in the medicament is a glycosaminoglycan. The medicament may be in particular to help clear mucus from the airways, particularly in COPD sufferers, preferably in such COPD sufferers displaying mucus hypersecretion.

Glycosaminoglycans are linear heteropolysaccharides possessing characteristic disaccharide repeat sequences that are typically highly N- and O-sulfated at D-glucosamine, galactosamine and uronic acid residues. These sulfate moieties introduce a high degree of negative charge along the glycosaminoglycan polymer chain and add to the heterogeneity of these macromolecules. In a preferred embodiment, the glycosaminoglycan may be to help thin mucus. The glycosaminoglycan may be to help expectoration or clearance of mucus.

Any suitable glycosaminoglycan may be employed in the invention.

Glycosaminoglycans and glycosaminoglycan salts suitable for use in the present invention may have an average molecular weight of from >8 to 40 kDa, preferably from 10 to 30 kDa, more preferably from 12 to 20 kDa. In particular, the glycosaminoglycan or salt may have an average molecular weight of from >12 to 18 kDa, preferably from 14 to 18 kDa, more preferably from 15 to 17 kDa and still more preferably from 16 to 17 kDa. In one instance, the glycosaminoglycan employed may have an average molecular weight which is above 8 kDa, 8.5 kDa, 9 kDa, 9.5 kDa, 10 kDa, or 11 kDa and in particular may have a molecular weight above 10 kDa. In one instance, the glycosaminoglycan may have an average molecular weight in a range with any of those values as the lower end of the range and, for instance any of the values specified herein as the upper end of the range, for example 18 kDa, 20 kDa, 30 kDa or 40 kDa as the upper end of the range. In one particularly preferred embodiment, the glycosaminoglycan employed is an unfractionated heparin having any of the average molecular weights or weight ranges specified herein. In some embodiments all, or substantially all, of the glycosaminoglycan molecules or glycosaminoglycan salt molecules will have a molecular weight falling within the ranges specified above. Thus from 50 to 100%, preferably from 75 to 100%, more preferably from 90 to 100%, still more preferably 95 to 100% of the molecules may have such a molecular weight. In some cases at least 95%, preferably at least 97.5%, more preferably at least 99%, still more preferably at least 99.5% and even more preferably at least 99.9% may have a molecular weight falling within the range. The glycosaminoglycan or salt thereof may be present in a range of molecular weight sizes and typically the most commonly occurring molecular weight size will fall within one of the above specified molecular weight ranges.

Typically, the glycosaminoglycan or salt thereof employed in the invention will be a long polymer. Preferably, the glycosaminoglycan or salt thereof will be at least 30 nm in length when fully extended. Even more preferably, the glycosaminoglycan or salt thereof will be at least 300 nm in length when fully extended. Still more preferably, the glycosaminoglycan will be at least 400 nm in length when fully extended. Because of their propensity to entangle, such extended molecules are anticipated to behave very differently in solution to typical small molecules (i.e. molecules that are <1000 Da in molecular weight). In particular, such extended molecules are anticipated to behave very differently in a viscous solution to typical small molecules.

Preferably, the glycosaminoglycan or salt thereof employed in the invention will be any of chondroitin sulfates A to E, heparin, unfractionated heparin, the sodium salt of heparin, heparin sulfate, heparan, heparan sulfate, hyaluronic acid, keratan sulfate, a derivative of any thereof or a mixture of any two or more thereof. Chondroitin sulfate B is sometimes referred to as dermatan sulfate. In a more preferred embodiment of the invention the glycosaminoglycan or salt thereof will be any of chondroitin sulfates A, C, D or E, heparin, unfractionated heparin, the sodium salt of heparin, heparin sulfate, heparan, heparan sulfate, hyaluronic acid, keratan sulfate, a derivative of any thereof or a mixture of any two or more thereof. In an even more preferred embodiment of the invention the glycosaminoglycan or salt thereof will be any of chondroitin sulfates A, C, D or E, heparin, unfractionated heparin, the sodium salt of heparin, heparin sulfate, heparan, heparan sulfate, keratan sulfate, a derivative of any thereof or a mixture of any two or more thereof. In a particularly preferred embodiment the glycosaminoglycan or salt thereof will be chondroitin sulfate A, chondroitin sulfate C, heparin, unfractionated heparin, the sodium salt of heparin, heparin sulfate, heparan, heparan sulfate, a derivative of any thereof or a mixture of any two or more thereof. In a still further preferred embodiment the glycosaminoglycan or salt thereof will be chondroitin sulfate A, chondroitin sulfate C, heparin, unfractionated heparin, the sodium salt of heparin, heparan sulfate, a derivative of any thereof or a mixture of any two or more thereof. More preferably, the glycosaminoglycan or salt thereof will be chondroitin sulfate A, chondroitin sulfate C, heparin, unfractionated heparin, the sodium salt of heparin, a derivative of any thereof or a mixture of any two thereof. In an even more preferred embodiment of the invention the glycosaminoglycan or salt thereof will be heparin, unfractionated heparin, the sodium salt of heparin, heparin sulfate or a derivative thereof. Still more preferably, the glycosaminoglycan or salt thereof will be heparin, unfractionated heparin, the sodium salt of heparin, or a derivative thereof. Even more preferably, the glycosaminoglycan or salt thereof will be heparin.

In some embodiments, the glycosaminoglycan or salt thereof will not be hyaluronic acid. In a preferred embodiment, the glycosaminoglycan or salt thereof also comprises sulfate moieties. For example, the glycosaminoglycan or salt thereof may comprise one, two, three, four, five, six or more sulfate moieties per tetrasaccharide repeating unit. Preferably, the glycosaminoglycan or salt thereof may comprise two or more sulfate moieties per disaccharide repeating unit, or four or more sulfate moieties per tetrasaccharide repeating unit. In a particularly preferred embodiment, the glycosaminoglycan or salt thereof comprises two sulfate moieties per disaccharide repeating unit, or four sulfate moieties per tetrasaccharide repeating unit. In a preferred embodiment, the glycosaminoglycan or salt thereof comprises sulfamate moieties. For example, the glycosaminoglycan or salt thereof may comprise one, two, three, four or more sulfamate moieties per tetrasaccharide repeating unit. Preferably, the glycosaminoglycan or salt thereof may comprise one or more sulfamate moieties per disaccharide repeating unit, or two or more sulfamate moieties per tetrasaccharide repeating unit. In a particularly preferred embodiment, the glycosaminoglycan or salt thereof comprises one sulfamate moiety per disaccharide repeating unit, or two sulfamate moieties per tetrasaccharide repeating unit. In a particularly preferred embodiment, the glycosaminoglycan or salt thereof comprises two sulfate moieties and one sulfamate moiety per disaccharide repeating unit, or four sulfate moieties and two sulfamate moieties per tetrasaccharide repeating unit.

As used herein, the term "sulfate moiety" refers to a functional group having the formula —O—SO$_3^-$ (in its unprotonated form) or —O—SO$_3$H (in its protonated form) and which is attached to the remainder of the molecule via a covalent linkage to one of the oxygen atoms of the sulfate moiety. As used herein, the term "sulfamate moiety" refers to a functional group having the formula —NH—SO$_3^-$ (in its unprotonated form) or —NH—SO$_3$H (in its protonated form) and which is attached to the remainder of the molecule via a covalent linkage to the nitrogen atom of the sulfamate moiety. For the avoidance of doubt, the terms "sulfate" and "sulfamate" are not interchangeable and are instead mutually exclusive terms. A "sulfate" moiety does not encompass a "sulfamate" moiety and a "sulfamate" moiety does not encompass a "sulfate" moiety.

In some embodiments of the invention the glycosaminoglycan employed will be a mixture of two glycosaminoglycans or salts thereof from one of the above mentioned groups. In other embodiments of the invention the glycosaminoglycan or salt thereof employed will be a mixture of more than two glycosaminoglycans or salts thereof from one of the above mentioned groups, such as a mixture of three, four or five of the glycosaminoglycans or salts thereof.

In embodiments of the invention where a mixture of two glycosaminoglycans or salts thereof is employed the two may, for example, be present in the ratio 1:1, 1:2, 1:4, 1:10 or 1:100. The ratio may be 90:10, 80:20, 70:30, or 60:40. Any suitable ratio may be employed and either glycosaminoglycan or salt thereof may be at the higher concentration. The ratio may be the same as the ratio in which the two are isolated when they are recovered from a common tissue using standard techniques.

Typically, the glycosaminoglycan or salt thereof will not have been subjected to fragmentation to reduce its molecular weight. Usually, the glycosaminoglycan or salt thereof will not have been subjected to depolymerisation, such as by chemical or enzymatic means, to reduce its molecular weight. The average number of saccharide units in the polysaccharide chains of the glycosaminoglycan may typically be from 18 to 100, preferably from 30 to 80, more preferably from 40 to 60 and still more preferably from 50 to 60 units.

The glycosaminoglycan or salt thereof may be any suitable commercially available glycosaminoglycan and may, for example, be an unfractionated glycosaminoglycan, particularly an unfractionated heparin having one of the molecular weights, or weight ranges, specified herein. The glycosaminoglycan or salt thereof will have typically been isolated from a natural source such as from an animal. In some cases, the glycosaminoglycan or salt thereof may be a synthetic glycosaminoglycan rather than be a naturally-occurring molecule.

In some cases the glycosaminoglycan or salt thereof may have been isolated from an animal, and in particular from animal tissues such as those of pigs or cattle. The glycosaminoglycan or salt thereof may have been obtained from tissues such as the lung, liver, or gut of an animal and in particular from beef lung or pork intestinal mucosa. The glycosaminoglycan or salt thereof may have been obtained from the skin of such an organism.

In some embodiments, the glycosaminoglycan or salt thereof may have been isolated from a cartilaginous fish or other sea or freshwater organism. In some cases the glycosaminoglycan may have been isolated from a shark or squid and in particular from the cartilage of such an organism. The glycosaminoglycan or salt thereof may have been isolated from a sturgeon and in particular from a sturgeon notochord.

One of the specific glycosaminoglycans mentioned above may have been modified to generate a derivative of the glycosaminoglycan. Thus such derivatives may be used in the invention as long as they retain therapeutic activity in treating a patient and in particular are capable of eliminating, reducing, ameliorating or managing one or more of the symptoms and manifestations of respiratory disease discussed herein. Thus in the case of heparin, the heparin may have been subjected to removal of sulfate groups from oxygen such as at least at the 2-O and 3-O positions. The same or equivalent modifications may be made to other glycosaminoglycans to generate derivatives for use in the present invention.

The glycosaminoglycan or salt thereof may have been subjected to acetylation, deacetylation, oxidation and/or decarboxylation such as, for example, periodate oxidation to generate a derivative. Heparinoids may be used in the invention.

Typically, the liquid medicament used in the present invention comprises a glycosaminoglycan or physiologically acceptable salt thereof comprising repeating disaccharide units of general formula (1):

-[A-B]-  (1)

wherein each A is the same or different and represents a moiety of formula (i) or (ii)

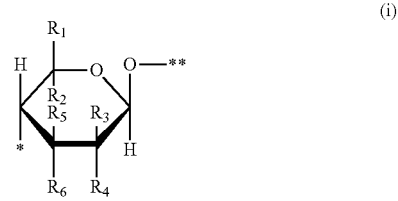

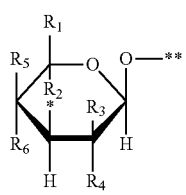

(ii)

or a physiologically acceptable salt thereof, wherein:
one of $R_1$ and $R_2$ is hydrogen, and the other is —$CO_2H$, —$SO_3H$ or —$CH_2OR$, wherein R is hydrogen or —$SO_3H$;
one of $R_3$ and $R_4$ is hydrogen, and the other is —OR, wherein R is hydrogen or —$SO_3H$;
one of $R_5$ and $R_6$ is hydrogen, and the other is —OH;
* represents a direct bond to an adjacent hydrogen atom or B moiety; and
** represents a direct bond to an adjacent B moiety,
and further wherein each B is the same or different and represents a moiety of formula (iii) or (iv)

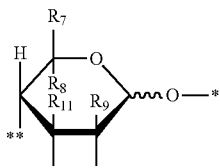

(iii)

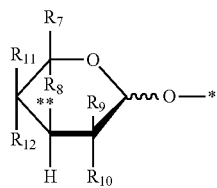

(iv)

or a physiologically acceptable salt thereof, wherein:
one of $R_7$ and $R_8$ is hydrogen and the other is —$CH_2OH$ or —$CH_2OSO_3H$;
one of $R_9$ and $R_{10}$ is hydrogen and the other is —NHAc, —$NH_2$ or —$NHSO_3H$;
one of $R_{11}$ and $R^{12}$ is hydrogen and the other is —OH or —$OSO_3H$;
∿∿∿ indicates a bond in either stereochemical orientation;
* represents a direct bond to a hydrogen atom or an adjacent A moiety; and
** represents a direct bond to an adjacent A moiety.

The formulae herein adopt standard practice in depicting sugars, using Haworth projections.

Preferably, each A moiety in the glycosaminoglycan of general formula (1) is a moiety of general formula (i).

Typically, one of $R_1$ and $R_2$ is hydrogen, and the other represents —$CO_2H$ or —$CH_2OR$, wherein R is hydrogen or —$SO_3H$. Preferably, one of $R_1$ and $R_2$ is hydrogen and the other represents —$CO_2H$.

Typically, $R_3$ is hydrogen and $R_4$ is —OR, wherein R represents hydrogen or —$SO_3H$. Typically $R_5$ is —OH and $R_6$ is hydrogen.

Typically each A is the same or different and represents a moiety of formula (i).

Typically $R_7$ is —$CH_2OH$ or —$CH_2OSO_3H$ and $R_8$ is hydrogen. Typically $R_9$ is hydrogen and $R_{10}$ is —NHAc, —$NH_2$ or —$NHSO_3H$. Typically Ru is —$OSO_3H$ or —OH and $R^{12}$ is hydrogen.

Typically each B is the same or different and represents a moiety of formula (v) or (vi)

(v)

(vi)

wherein $R_7$, $R_8$, $R_9$, $R_{10}$, $R_{11}$, $R_{12}$, * and ** are as described above.

Preferably $R_1$ is not hydrogen in an A moiety which is adjacent to a moiety (iv) in which $R^{12}$ is hydrogen.

Typically the glycosaminoglycan of general formula (1) is a glycosaminoglycan of general formula (2)

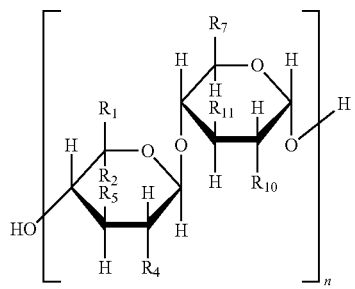

(2)

wherein:
one of $R_1$ and $R_2$ is hydrogen and the other is —$CO_2H$;
$R_4$ is —OH or —$OSO_3H$;
$R^5$ is —OH;
$R_7$ is —$CH_2OH$ or —$CH_2OSO_3H$;
$R_{10}$ is —$NH_2$, —$NHSO_3H$ or —NHAc; and
$R_{11}$ is —$OSO_3H$ or OH;
preferably wherein:
$R_1$ is hydrogen and $R_2$ is —$CO_2H$;
$R_4$ is —$OSO_3H$;
$R^5$ is —OH;
$R_7$ is —$CH_2OSO_3H$;
$R_{10}$ is —$NHSO_3H$; and
$R_{11}$ is —OH.

Typically the glycosaminoglycan of general formula (1) is a glycosaminoglycan of general formula (3)

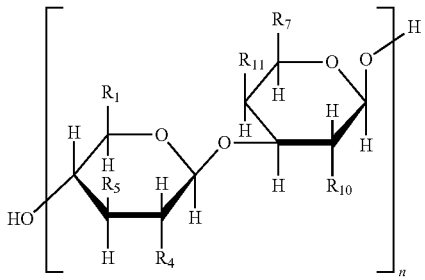

wherein:
$R^1$ is —$CO_2H$;
$R^4$ is —OH;
$R^5$ is —OH;
$R_7$ is —$CH_2OH$ or —$CH_2OSO_3H$;
$R_{10}$ is —NHAc; and
Rn is —OH or —$OSO_3H$.

Typically the glycosaminoglycan of general formula (1) is a glycosaminoglycan of general formula (4)

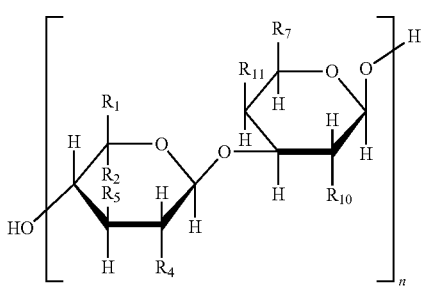

wherein:
one of $R_1$ and $R_2$ is hydrogen and the other is —$CO_2H$;
$R_4$ is —OH or —$OSO_3H$;
$R_5$ is —OH;
$R_7$ is —$CH_2OH$ or —$CH_2OSO_3H$;
$R_{10}$ is —NHAc; and
$R_{11}$ is —OH or —$OSO_3H$.

Alternatively, the glycosaminoglycan of general formula (1) may be a glycosaminoglycan of general formula (5)

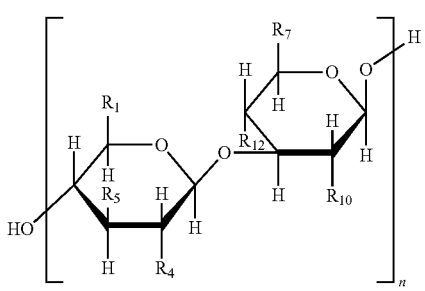

wherein:
$R_1$ is —$CO_2H$;
$R_4$ is —OH;
$R_5$ is —OH;
$R_7$ is —$CH_2OH$;
$R_{10}$ is —NHAc; and
$R_{12}$ is —OH.

However, in a preferred embodiment, the glycosaminoglycan of general formula (1) is not a glycosaminoglycan of general formula (5).

Any suitable physiologically acceptable glycosaminoglycan salt may be employed in the invention and in particular a metallic salt, for example a sodium salt, an alkali metal salt or an alkaline earth metal salt. Other salts include calcium, lithium and zinc salts. Ammonium salts may also be used. The salt may be a sodium glycosaminoglycanate or glycosaminoglycan sulfate. Salts of derivatives of specific glycosaminoglycans mentioned herein may also be used in the invention. In the present application where mention of a glycosaminoglycan is made, such mention also includes physiologically acceptable salts thereof.

Typically a physiologically acceptable salt is a salt with a physiologically acceptable acid or base. Preferred salts are salts with physiologically acceptable bases. Typically, such salts are compounds wherein the acidic hydrogen atom of a —$CO_2H$ and/or —$OSO_3H$ group is replaced with a cation, for example an alkali metal (e.g. sodium or potassium) or alkaline earth metal (e.g. calcium or magnesium) cation. Such salts can be prepared, for example, by reaction with an appropriate hydroxide.

The number of disaccharide units present in the glycosaminoglycan or salt thereof employed in the invention will be such that the molecular weight of the glycosaminoglycan or salt is from >8 to 40 kDa, preferably from 10 to 30 kDa, more preferably from 12 to 20 kDa. In particular, it may be such that the glycosaminoglycan has a molecular weight of from 12 to 18 kDa, preferably from 12 to 16 kDa and more preferably from 12 to 15 kDa. The number of disaccharide units present in the glycosaminoglycan may be represented by the number n, where n is any integer such that the glycosaminoglycan has a molecular weight falling within any of the above mentioned molecular weight ranges.

Thus the glycosaminoglycan or salt thereof employed may be represented by the general formula:

$$HO\text{-}[A\text{-}B]_n\text{-}H$$

wherein A-B is any of the disaccharide units mentioned above and n is an integer such that the glycosaminoglycan or salt thereof has a molecular weight falling within the above specified molecular weight ranges. The value of n may be, for example, from 12 to 55, and more preferably from 18 to 27.

The glycosaminoglycan employed in the invention will typically comprise more than one length chain. Hence n for some of the glycosaminoglycan chains present may be a lower or higher integer than an integer which, on its own, would give a chain of molecular weight size falling within one of the above specified ranges. Thus the average value of n of the glycosaminoglycans present in the liquid medicament used in the invention may be any of the values specified for n herein and in particular a value of n which gives a molecular weight glycosaminoglycan or salt thereof falling within one of the molecular weight ranges specified herein.

Particularly preferred salts for use in the invention are salts of formula:

$$HO\text{-}[A\text{-}B]_n^{x-}\text{-}H\ M^{x+}$$

wherein M represents a physiologically acceptable cation or a mixture thereof, and x is an integer value.

In a particularly preferred embodiment of the invention the glycosaminoglycan employed will be a heparin, derivative thereof or a physiologically acceptable salt thereof. Heparin is a naturally occurring mucopolysaccharide present in a variety of organs and tissues, particularly liver, lung, and the large arteries. Heparin is a polymer of alternating α-D-glucosamine and hexuronate residues joined by [1,4]-glycosidic linkages. When glycosaminoglycans are synthesised in nature, typically they are conjugated to a central protein core. However, preferably the glycosaminoglycans present in the liquid medicament will lack such a central core. Typically, glycosaminoglycan preparations will lack a core and may be employed or, if present, the core can be removed. Commercially available preparations of glycosaminoglycans will usually lack the core and may be employed.

Heparin is clinically used as an anti-coagulant, where it is thought to exert its effects through interaction with anti-thrombin III (AT-III) and heparin co-factor II and other coagulation factors. Typically the heparin will retain some anticoagulant activity, i.e. be able to increase clotting time in an individual. Thus preferably the heparin will be able to bind anti-thrombin III (AT-III) and/or heparin co-factor II (HCII) and hence inhibit clotting. Preferably it will be able to form a complex with AT-III, thrombin and a clotting factor. However, in some embodiments a heparin which lacks anti-coagulant activity or which has reduced anti-coagulant activity may also be employed. Thus the heparin may have been modified so that it has from 0 to 80%, preferably from 5 to 60%, more preferably from 10 to 40% and even more preferably from 10 to 30% of the activity of the unmodified form or in comparison to unmodified heparin. Other glycosaminoglycans, in particular dermatan sulfate, also possess anticoagulant activity. Preferably, therefore, the glycosaminoglycans and their derivatives employed will retain some anti-coagulant activity, as discussed above for heparin and its derivatives.

The liquid medicament comprising the glycosaminoglycan or physiologically acceptable salt thereof will typically be administered via inhalation. Preferably, therefore, the physicochemical properties of the liquid medicament will be compatible with use in a vibrating mesh nebuliser. Specifically, the physicochemical properties of the liquid medicament are such that an aerosol can be generated in the vibrating mesh nebuliser when the liquid medicament is present in the reservoir and the vibratable membrane is induced to vibrate. Preferably, the liquid medicament comprises an aqueous solution. The medicaments of the invention may also be provided in devices for delivery intranasally or via instillation and also in supply containers for such devices.

In one embodiment of the present invention, the concentration of the glycosaminoglycan or physiologically acceptable salt thereof in the liquid medicament is from 10 to 50 mg/mL. In other embodiments, the concentration is from 10 to 45 mg/mL, from 10 to 40 mg/mL, from 10 to 35 mg/mL, from 15 to 50 mg/mL, from 15 to 45 mg/mL, from 15 to 40 mg/mL, from 15 to 35 mg/mL, from 20 to 50 mg/mL, from 20 to 45 mg/mL, from 20 to 40 mg/mL, from 20 to 35 mg/mL, from 25 to 50 mg/mL, from 25 to 45 mg/mL, or from 25 to 40 mg/mL. Preferably, the concentration is from 25 to 35 mg/mL. More preferably, the concentration is about 30 mg/mL.

In another embodiment of the present invention, the liquid medicament further comprises an inorganic salt. Said inorganic salt may be any salt acceptable for use in the preparation of a medicament. Examples of such salts include, but are not limited to, the halides, oxides, hydroxides, sulfates, carbonates, phosphates, nitrates, acetates and oxamates of the alkali metals, alkaline earth metals, aluminium, zinc and ammonium. In some embodiments, said inorganic salt may be selected from the group consisting of sodium chloride, potassium chloride, magnesium chloride, calcium chloride, and ammonium chloride. In some embodiments, the inorganic salt is sodium chloride or magnesium chloride.

In some embodiments of the present invention, the inorganic salt is present in the liquid medicament in a total concentration of at least 10 mM. In some embodiments, the concentration of the inorganic salt in the liquid medicament is from 10 to 300 mM. In other embodiments, the concentration of the inorganic salt in the liquid medicament is from 10 to 250 mM, from 10 to 200 mM, from 25 to 300 mM, from 25 to 250 mM, from 25 to 200 mM, from 50 to 300 mM, from 50 to 250 mM, from 50 to 200 mM, from 75 to 300 mM, from 75 to 250 mM, from 75 to 200 mM, from 100 to 300 mM, or from 100 to 250 mM. Preferably, the concentration of the inorganic salt in the liquid medicament is from 100 to 200 mM. Even more preferably, the concentration of the inorganic salt in the liquid medicament is about 140 mM.

In some embodiments of the present invention, the viscosity of the liquid medicament is greater than 1.1 mPa·s. In other embodiments, the viscosity of the liquid medicament is greater than 1.5 mPa·s, or greater than 1.6 mPa·s, or greater than 1.75 mPa·s, or greater than 1.92 mPa·s, or greater than 1.98 mPa·s. Preferably, the viscosity of the liquid medicament is greater than 1.6 mPa·s. More preferably, the viscosity of the liquid medicament is greater than 1.92 mPa·s, or greater than 1.98 mPa·s. In some embodiments, the viscosity of the liquid medicament is less than 4.0 mPa·s. In other embodiments, the viscosity of the liquid medicament is less than 3.0 mPa·s, or less than 2.45 mPa·s, or less than 2.25 mPa·s. The viscosity may be about any of these values. In some embodiments, the viscosity of the liquid medicament is from 1.1 to 4.0 mPa·s, from 1.1 to 3.0 mPa·s, from 1.1 to 2.45 mPa·s, from 1.1 to 2.25 mPa·s, from 1.5 to 4.0 mPa·s, from 1.5 to 3.0 mPa·s, from 1.5 to 2.45 mPa·s, from 1.5 to 2.25 mPa·s, from 1.6 to 4.0 mPa·s, from 1.6 to 3.0 mPa·s from 1.6 to 2.45 mPa·s, from 1.6 to 2.25 mPa·s, from 1.75 to 4.0 mPa·s, from 1.75 to 3.0 mPa·s, from 1.75 to 2.45 mPa·s, from 1.75 to 2.25 mPa·s, from 1.92 to 4.0 mPa·s, from 1.92 to 3.0 mPa·s, from 1.92 to 2.45 mPa·s, from 1.92 to 2.25 mPa·s, from 1.98 to 4.0 mPa·s, from 1.98 to 3.0 mPa·s, from 1.98 to 2.45 mPa·s, or from 1.98 to 2.25 mPa·s. Preferably, the viscosity is from 1.6 to 3.0 mPa·s. More preferably, the viscosity is from 1.92 to 2.45 mPa·s. Even more preferably, the viscosity is from 1.98 to 2.45 mPa·s.

In preferred embodiments of the present invention, the liquid medicament comprises an aqueous solution of heparin, heparin sulfate, unfractionated heparin or a physiologically acceptable salt thereof. In some embodiments of the present invention, the liquid medicament comprises an aqueous solution of heparin, heparin sulfate, unfractionated heparin or salt thereof wherein the concentration of the heparin, heparin sulfate, unfractionated heparin or salt thereof is from 10 to 50 mg/mL. Optionally, the viscosity of said liquid medicament may be greater than 1.1 mPa·s. Optionally, the viscosity of said liquid medicament may also be less than 4.0 mPa·s. Optionally, said liquid medicament may also comprise an inorganic salt in a concentration of from 10 to 300 mM, preferably wherein the inorganic salt is sodium chloride or magnesium chloride. In other embodiments, the liquid medicament comprises an aqueous solution of heparin, heparin sulfate, unfractionated heparin or salt thereof wherein the concentration of the heparin, heparin sulfate, unfractionated heparin or salt thereof is from 20 to 40 mg/mL. Optionally, the viscosity of said liquid medicament may be greater than 1.6 mPa·s. Optionally, the viscosity of said liquid medicament may also be less than 4.0 mPa·s. Optionally, said liquid medicament may also comprise an inorganic salt in a concentration of from 25 to 250 mM, preferably wherein the inorganic salt is sodium chloride or magnesium chloride. In other embodiments, the liquid medicament comprises an aqueous solution of heparin, heparin sulfate, unfractionated heparin or salt thereof wherein the concentration of the heparin, heparin sulfate, unfractionated heparin or salt thereof is from 25 to 35 mg/mL. Optionally, the viscosity of said liquid medicament may be greater than 1.92 mPa·s. Optionally, the viscosity of said liquid medicament may also be less than 3.0 mPa·s. Optionally, said liquid medicament may also comprise an inorganic salt in a concentration of from 50 to 200 mM, preferably wherein the inorganic salt is sodium chloride or magnesium chloride. In other embodiments, the liquid medicament comprises an aqueous solution of heparin, heparin sulfate, unfractionated heparin or salt thereof wherein the concentration of the heparin, heparin sulfate, unfractionated heparin or salt thereof is from 25 to 35 mg/mL. Optionally, the viscosity of said liquid medicament may be greater than 1.98 mPa·s. Optionally, the viscosity of said liquid medicament may also be less than 2.45 mPa·s. Optionally, said liquid medicament may also comprise an inorganic salt in a concentration of from 100 to 200 mM, preferably wherein the inorganic salt is sodium chloride or magnesium chloride.

The invention provides a nebuliser loaded with any of the medicaments discussed herein, as well as a supply container loaded with such a medicament, particularly a nebuliser or container wherein the viscosity of the liquid medicament has any of the above values.

Supply Container and Kit

In some embodiments, the present invention provides a vibrating mesh nebuliser that is a disposable device. In other embodiments, the present invention provides a vibrating mesh nebuliser that is a reusable device. Preferably, the vibrating mesh nebuliser is a reusable device. In some embodiments, the reservoir holding the liquid medicament may be detachable from the remainder of the vibrating mesh nebuliser. Between uses of the nebuliser, the user may remove the reservoir and replace it with a supply container (e.g. a refill cartridge) comprising a liquid medicament, for instance to act as a fresh reservoir. Said supply container may be structurally similar to the reservoir, or identical to it, or it may be structurally different to the reservoir. In other embodiments, the reservoir has a liquid medicament inlet port. The amount of liquid medicament present in the reservoir may be increased by supplying additional amounts of liquid medicament to the reservoir from a supply container comprising the liquid medicament via the liquid medicament inlet port. In some embodiments, the reservoir holding the liquid medicament may not be detachable from the remainder of the vibrating mesh nebuliser.

The present invention therefore also provides a supply container for delivering a liquid medicament to a vibrating mesh nebuliser according to the invention, wherein the supply container comprises a liquid medicament as defined above. In some embodiments, the invention provides a supply container for delivering a liquid medicament to the reservoir of the vibrating mesh nebuliser. In other embodiments, the invention provides a supply container for delivering a liquid medicament to the vibrating mesh nebuliser by replacement of the reservoir of the nebuliser with the supply container. The present invention further provides any container or cartridge used to load a device described herein, which container or cartridge comprises a medicament of the invention.

The present invention further provides a kit for delivery of a medicament to a respiratory system, the kit comprising:
 (a) a vibrating mesh nebuliser, wherein the vibrating mesh nebuliser is a vibrating mesh nebuliser according to the invention or a vibrating mesh nebuliser that is not loaded with liquid medicament; and
 (b) one or more liquid medicament supply container(s) as defined above.

A kit according to the invention may further comprise instructions for use of the vibrating mesh nebuliser and/or supply container. These instructions may contain information on the recommended frequency or timing of use of the nebuliser by a patient in need thereof, how to use the nebuliser, how to replace or refill the reservoir comprising the liquid medicament and other advice. A kit according to the invention may also comprise packaging.

The present invention also provides a method of loading a vibrating mesh nebuliser with liquid medicament from a supply container according to the invention, wherein the method involves inserting said supply container into a vibrating mesh nebuliser which is not loaded with a liquid medicament, or wherein the method involves dispensing the liquid medicament from said supply container into a vibrating mesh nebuliser which is not loaded with a liquid medicament.

Loading a nebuliser of the invention may, for instance, entail filling, or refilling, the reservoir of the nebuliser with a composition of the invention using a supply container as described herein. A supply container of the invention may, for instance, include means for allowing or facilitating such loading into the reservoir. In a further instance, loading may entail replacing the reservoir already in the nebuliser with a supply container comprising a composition of the invention. In such instances, effectively the supply container is a reservoir and each time a nebuliser becomes empty it can be reloaded by replacing the existing reservoir with a new one. Such loading or reloading of a reservoir in a nebuliser or loading a supply container or reservoir into a nebuliser is also provided by the present invention. Supply containers or reservoirs may be shaped appropriately and/or be adapted to allow them to be loaded into the nebuliser. The present invention also provides a method for loading supply containers or reservoirs which are separate to a nebuliser, comprising dispensing a composition of the invention into such a container or reservoir.

Therapy of Patients

The vibrating mesh nebuliser according to the present invention is useful in the delivery of a medicament comprising a glycosaminoglycan or physiologically acceptable salt thereof to the respiratory system of a patient in need thereof. In some embodiments, the patient in need thereof is a patient with a respiratory disease or condition. In some embodiments, the respiratory disease or condition is COPD. The Global Initiative for Chronic Obstructive Lung Disease (GOLD), a project initiated by the National Heart, Lung, and Blood Institute (NHLBI) and the World Health Organization (WHO), defines COPD as follows: "Chronic obstructive pulmonary disease (COPD), a common preventable and treatable disease, is characterized by persistent airflow limitation that is usually progressive and associated with an enhanced chronic inflammatory response in the airways and the lung to noxious particles or gases. Hence, the patient may be one who meets the criteria set out in the GOLD guidelines for a diagnosis of COPD. Exacerbations and comorbidities contribute to the overall severity in individual patients." COPD may also be referred to as chronic airflow limitation (CAL).

Accordingly, the present invention provides a composition for use in a method of treatment of a disease in a patient by therapy, in which method (i) the patient is treated by administering the composition to the respiratory system, and (ii) the composition is delivered to the respiratory system by a vibrating mesh nebuliser according to the invention, wherein the composition comprises a compound which is a glycosaminoglycan or a physiologically acceptable salt thereof.

The present invention also provides a method of treatment of a disease in a patient by therapy, in which method (i) a composition is administered to the respiratory system of the patient in order to treat the patient, and (ii) the composition is delivered to the respiratory system by a vibrating mesh nebuliser according to the invention, wherein the composition comprises a compound which is a glycosaminoglycan or a physiologically acceptable salt thereof.

Said compound may be any suitable glycosaminoglycan or physiologically acceptable salt thereof, as described herein in the section above pertaining to liquid medicaments of the invention. In one particularly preferable embodiment of the invention, the compound is selected from the group consisting of heparin, unfractionated heparin, the sodium salt of heparin, heparin sulfate, and a derivative of any thereof.

In some embodiments of the invention, the method of treatment may further comprise administration of a therapeutic agent and/or DNase to the patient, in addition to administration of the glycosaminoglycan. Said therapeutic agent may be any suitable therapeutic agent, as described below in the section pertaining to liquid medicaments further comprising a therapeutic agent. Said DNase may be any suitable DNase, as described below in the section pertaining to liquid medicaments further comprising a DNase.

In one embodiment, the therapeutic agent and/or DNase may be co-administered with the glycosaminoglycan from the same vibrating mesh nebuliser. In another embodiment, the therapeutic agent and/or DNase may be administered from a different vibrating mesh nebuliser to the glycosaminoglycan. In a further embodiment, the therapeutic agent and/or DNase may be administered to the patient via a different method of administration to the glycosaminoglycan. Preferably, the method of administration of the therapeutic agent and/or DNase is intranasal, via inhalation and/or via instillation. The therapeutic agent and/or DNase may be administered to the patient before, at the same time as, or after the glycosaminoglycan.

In a preferred embodiment, the patient to be treated is an ambulatory patient or a patient not requiring mechanical ventilation. In an alternative embodiment, the patient to be treated is not an ambulatory patient.

In some embodiments of the invention, the disease to be treated is a respiratory disease. In preferred embodiments, the respiratory disease is characterised by mucous hyper secretion or elevated mucous viscosity. More preferably, the respiratory disease is selected from the group consisting of chronic obstructive pulmonary disease, emphysema, cystic fibrosis, bronchitis, asthma, bronchiectasis, primary ciliary dyskinesia, pneumonia, sinusitis, sinus congestion, influenza and a cold. In some embodiments, the respiratory disease is chronic obstructive pulmonary disease. In some embodiments, the respiratory disease is emphysema. In some embodiments, the respiratory disease is cystic fibrosis. In some embodiments, the respiratory disease is bronchitis. A patient to be treated may also, or alternatively, have a history of exposure to pollutants such as tobacco smoke or allergens such as pollen. A patient to be treated may use inhaled drugs such as, for example cannabis or other drugs commonly mixed with tobacco before smoking. A patient to be treated may have additionally been, or alternatively been, exposed to other chemical or environmental pollutants, for example occupational dusts and chemicals (vapours, irritants and fumes), indoor or outdoor air pollution, particulate matter, irritants, vehicle exhaust emissions, smog, sulfur dioxide, organic dusts and sensitising agents. The patient may work, or have worked, in an environment which exposes them to chemicals and/or pollutants.

In one particularly preferred embodiment, the glycosaminoglycan or salt thereof acts as a mucolytic. In this embodiment, the method of treatment further comprises reducing the viscosity of mucous in the respiratory system of the patient. In another embodiment, the glycosaminoglycan or salt thereof does not act as a mucolytic. In some embodiments, the glycosaminoglycan or salt thereof has an anticoagulant effect. In other embodiments, the glycosaminoglycan or salt thereof does not have an anticoagulant effect. In particularly preferred embodiments, the glycosaminoglycan is heparin, heparin sulfate, unfractionated heparin, the sodium salt of heparin, or a derivative of any thereof.

For the purposes of the present invention COPD may be defined as a condition where there is a progressive decline in lung function, with a patient affected by COPD having an $FEV_1$ of less than 80% of that predicted for an individual of that age/race and/or height and/or who displays a $FEV_1/FVC$ ratio of less than 70%. In an especially preferred embodiment, the patient to be treated will have an $FEV_1$ of less than 75% of that predicted.

Typically the reduction of $FEV_1$ is only partially reversible. In particular the reduction in $FEV_1$ is only partially reversible by treatment with bronchodilators such as, for example, $\beta_2$ adrenergic agonists and in particular salbutamol.

$FEV_1$ is defined as the maximal forced volume which can be expired in one second starting from maximum inspiration [11]. It can be measured by standard techniques well known in the art, e.g. by spirometry. The $FEV_1$ for an individual may be from 10 to 80% of that predicted. Typically, the $FEV_1$ of the patient will be from 10 to 75% of the predicted value. Preferably the patient may have a $FEV_1$ of from 60 to 75% the predicted value, more preferably from 40 to 60% of predicted and even more preferably a value below 40% of that predicted. The patient may have an $FEV_1$ of less than 70%, preferably less than 60%, more preferably less than 50% and even more preferably less than 40% of that predicted. The patient may typically have a history of exposure to pollutants or chemicals and in many cases will be, or have been, a tobacco smoker. In an alternative embodiment, the patient may be suffering from mild respiratory disease. Typically, such patients will have an $FEV_1$ of greater than 80%. Such patients constitute a patient group that is at risk of developing more severe COPD.

The $FEV_1$ value for the patient will normally be measured against predicted values and adjusted for age/sex/race and/or height. Predicted values may be those taken from Coates (supra, [11]). The expected value, which the value obtained for the patient may be compared to, may be the average expected value for smokers, or non-smokers, or both groups combined, preferably the expected value will be that for non-smokers not suffering from CAL (Coates, supra, [11]).

The reduction in $FEV_1$ in the patient will only be partially reversible and in particularly only be partially reversible on administration of a bronchodilator. Thus, for example, an increase in $FEV_1$ over the base-line value for the patient (i.e. that prior to administration of the bronchodilator) of more than 15%, preferably more than 20% and even more preferably over 25% will be regarded as reversibility. The increase may begin from 5 to 30, preferably from 10 to 25, more preferably over a period of from 15 to 20 minutes after the administration of the bronchodilator. Preferably the increases will begin from 15 minutes after the administration of the bronchodilator. The increases persist typically from 3 to 6 hours, preferably from 4 to 5 hours and more preferably 4 hours. Typically the bronchodilator used in assessing reversibility will be a $\beta_2$ adrenergic agonist such as salbutamol, or ipratropium. In one embodiment the reduction in $FEV_1$ may be totally, or almost totally refractory to treatment with bronchodilators.

The patient may also show similar minimal increases in $FEV_1$ with steroid drugs such as budesonide, prednisolone or fluticasone, although typically response to such agents will not be used to define reversibility. The increases will also occur over a longer time period such as after 2 to 3 days and, if the steroid drugs are continually administered, persist. If steroids are stopped the improvement may persist for from 12 to 48 hours, or for days, weeks or even months, such as from six hours to six weeks, preferably from 1 day to 3 weeks.

Tests to assess reversibility of reduction of $FEV_1$ will typically be performed when the patient is clinically stable and free from infection. The patient should not have taken, or have had administered to them, inhaled short-acting bronchodilators in the previous six hours, long-acting $\beta$ agonists in the previous 12 hours or sustained release theophyllines in the preceding 24 hours.

Spirometric values should typically be measured before and after an adequate dose of inhaled bronchodilator is given to the patient. The dose should preferably be selected to be high on the dose/response curve and usually will be given by nebuliser to be certain it has been inhaled. A similar dose may be given with multiple inhalations from a metered dose inhaler and large volume spacer, but this is less preferred. A typical dosage/measurements protocol for a human patient would be:

before and 15 minutes after 2.5 to 5 mg nebulised salbutamol or 5 to 10 mg terbutaline;
before and 30 minutes after 500 µg nebulised ipratropium bromide; or
before and 30 minutes after both in combination.

The FVC (forced vital capacity) of the patient may also be measured in the diagnosis of COPD. The ratio of $FEV_1$ to FVC can be used in the diagnosis of COPD. Patients to be treated will typically have an $FEV_1/FVC$ value of less than 70%. The ratio of $FEV_1/FVC$ may be below 65%, preferably below 60%, more preferably below 55% and even more preferably below 55%. In an especially preferred embodiment, a patient will have a $FEV_1/FVC$ of below 70% and also have a $FEV_1$ value of 80% or less of that predicted.

FVC corresponds to the maximal volume of air forcibly exhaled from the point of maximal inhalation and can be measured using standard spirometry. In particular, the above specified values for $FEV_1/FVC$ will be those after administration of a bronchodilator as outlined above. The reduction in $FEV_1/FVC$ will typically show the same lack of reversibility as $FEV_1$.

Spirometric assessment is the most preferred method for diagnosing COPD and hence method for identification of patients who may be treated. Accordingly, in an especially preferred embodiment of the invention spirometric assessment will be used in the diagnosis of a patient who has COPD and hence is treatable using the invention. In addition, the symptoms displayed by the patient may also be assessed to help confirm a diagnosis of COPD. Typically diagnosis will involve spirometric assessment in combination with assessment of the symptoms of a patient as well as elucidating whether the patient has a history of exposure to risk factors. In some situations spirometric assessment may not be possible, particularly in situations where resources are limited, and COPD will be diagnosed by alternative means such as by looking for the symptoms of COPD described below and a history of exposure to risk factors for COPD. Although chest X-rays are not typically indicative of whether or not a patient has COPD, they may be used to diagnose other respiratory disorders, such as TB, and hence rule out COPD.

The patient may typically show, or have previously shown, an accelerated rate of decline of lung function compared to the average expected for an equivalent individual not suffering from COPD and in particular for an equivalent non-smoking individual. The patient may display shortness of breath and in particular may do so after physical exertion such as on exercise. Typically, this will not be induced by exposure to an allergen. The patient may also show increased incidence of bacterial or viral infection and this may exacerbate the condition.

The individual may show a rate of decrease in $FEV_1$ one, two, three, four or more times greater than the average annual value expected for an equivalent individual not suffering from COPD. For instance a patient over thirty may show an annual reduction of from 50 to 100, preferably from 50 to 80 and more preferably from 60 to 70 ml $FEV_1/yr$ compared to a reduction of from 10 to 40 and typically of 20 to 40 ml of $FEV_1/yr$ in the equivalent non-smoker. These values may also apply to non-smoking sufferers of COPD such as where the disorder is caused by pollutants.

Patients with COPD may display one or more, and sometimes all, of cough, increased sputum production, dyspnea, and/or a history of exposure to risk factors for the disease. In the case of cough, increased sputum and dyspnea these may have been present for extended periods of time such as at least a month, preferably six months, more preferably at least a year and still more preferably for at least two years. Chronic cough and sputum production often precede the development of COPD and may be indicative of individuals for which the invention can be used prophylactically to prevent the development of COPD.

In one embodiment, the present invention provides a compound for use in a method of treatment of COPD in a human patient who has mucus hypersecretion, wherein the compound is a glycosaminoglycan or physiologically acceptable salt thereof, and in which method (i) the patient is treated by administering the compound to the respiratory system, (ii) the compound is delivered to the respiratory system by a vibrating mesh nebuliser according to the invention, and (iii) the compound facilitates the clearance of mucus from the central and peripheral airways of the patient. In a preferred embodiment, the glycosaminoglycan is heparin, unfractionated heparin, the sodium salt of heparin, heparin sulfate, or a derivative of any thereof. In a further preferred embodiment, the patient has an $FEV_1$ of from 10 to 80% of the predicted value for an equivalent patient not suffering from COPD. More preferably, the patient has an FEV$_1$ of from 20 to 50% of the predicted value. In another embodiment, the patient may be suffering from a bacterial or viral infection. In another embodiment, the compound facilitates a reduction in mucus plugging in the patient.

The compound for use according to the present invention is formulated as an aerosol. The aerosol particle size and/or other properties of the aerosol particle may be chosen to ensure that the particles are delivered to a particular region of the respiratory tract. For example, they may be designed to reach only the upper or lower parts of the respiratory tract. In cases where the glycosaminoglycan or physiologically acceptable salt thereof, or a therapeutic agent or DNase, are delivered as an aerosol in an aqueous form, the solution will preferably be isotonic to help ensure effective delivery to the patient. In particular, particles with a diameter of less than 10 m are thought to be effective in reaching the lower parts of the respiratory tract and hence may be employed where such a site is the desired target for the medicaments. In embodiments where it is desired to deliver the compound for use according to the invention to the lower parts of the respiratory tract, e.g. alveoli, the mass median aerodynamic diameter (MMAD) of the particles administered may be less than 10 μm, preferably less than 8 μm, more preferably less than 6 μm and even more preferably less than 5 μm. The MMAD (also known as D$_{50}$ value) is the value of the particle diameter for which, when all particles in a sample are arranged in order of ascending mass, 50% of the total mass of the particles is in particles having a diameter less than the MMAD.

In one embodiment the particles may have an MMAD of 3 μm or less. In another embodiment the particles may have an MMAD of 2 μm or less. In an especially preferred embodiment, the particles will have a diameter of from 1 to 5 μm. In some cases the particles administered may be less than 1000 nm, or less than 500 nm, or less than 250 nm or less than 100 nm in diameter. The sizes may refer to particles of solid matter or droplets of solutions and suspensions.

The nominal dose of the compound for use in a method of the present invention to be administered will normally be determined by a physician, but will depend upon a number of factors such as the nature of the condition to be treated and the condition of the patient. The dose of glycosaminoglycan administered may, for example, be from 0.01 mg to 5 g, preferably from 0.1 mg to 2.5 g, more preferably from 1 mg to 1 g, even more preferably from 10 mg to 500 mg, still more preferably from 50 mg to 250 mg and even more preferably from 100 mg to 250 mg. These doses will typically be given once, twice or three times a day and will preferably be given once or twice a day and more preferably will be given twice a day. The actual dose delivered to the respiratory system of the patient may be at least 20% of the nominal dose, more preferably at least 25% of the nominal dose, and even more preferably at least 30% of the nominal dose. In some embodiments, the actual dose delivered to the respiratory system of the patient may be at least 40% of the nominal dose. Typically, the actual dose will be delivered to the respiratory system of the patient over a time period of from 5 to 15 minutes.

For heparin and derivatives thereof and salts of either, the nominal dose will typically be in the range of from 10 to 10,000 units per kg body weight, preferably 100 to 2,000 units per kg body weight, more preferably from 250 to 1000 unit per kg body weight, and even more preferably from 500 to 800 units per kg body weight. A unit of heparin activity is defined by the United States Pharmacopeia as the amount of heparin that prevents 1 mL of citrated sheep plasma from clotting for one hour after adding 0.2 mL of 1% aqueous CaCl$_2$. These doses will typically be given once, twice or three times a day and will preferably be given twice a day.

The length of treatment may typically be from two days, two weeks, a month, six months, a year or more. In many cases the patient will continue to use the compound for use according to the invention permanently or for extended periods. This may in particular be the case where the patient is a smoker who does not stop smoking or continues to be exposed to a chemical pollutant thought to be the causative agent of respiratory disease. This may also be the case where the patient has a genetic predisposition to developing COPD and most likely will need the medicament indefinitely. The treatment schedule may also be coordinated so that at times when the respiratory disease increases in severity, such as times, or periods, of increased breathlessness and/or inflammation, the dose of glycosaminoglycan given is elevated or these may be the main times that glycosaminoglycan is administered. The compound for use according to the invention may be administered prior to exercise or physical exertion and may typically be given as an aid to physiotherapy. It may be administered during infections or when an infection is suspected. In any of the embodiments discussed herein the subject may have an infection and in particular one of the respiratory system. Such an infection may be the disorder to be treated on its own or alternatively may be present as well as one of the other disorders discussed herein. An infection may be, for instance, present and exacerbate any of the conditions mentioned herein. For instance, the subject may have a viral infection, a bacterial infection or a fungal infection.

Liquid Medicaments Further Comprising a Therapeutic Agent or a DNase

In one preferred embodiment the medicament may comprise the glycosaminoglycan as the sole therapeutic agent. However, in a further preferred embodiment a different (second) therapeutic agent may also be present. When a second therapeutic agent is present in addition to the glycosaminoglycan, in some embodiments both the second therapeutic agent and the glycosaminoglycan are intended to have a therapeutic effect. In other embodiments, only the second therapeutic agent is intended to have a therapeutic effect and the glycosaminoglycan is not intended to have a therapeutic effect. In some embodiments, the glycosaminoglycan is intended to facilitate delivery of the second therapeutic agent to its target site in the body. In one embodiment of the present invention, the liquid medicament present in the vibrating mesh nebuliser further comprises a second therapeutic agent and/or a DNase, in addition to the glycosaminoglycan or salt thereof. Alternatively, the liquid medicament may further comprise a non-therapeutic agent, in addition to the glycosaminoglycan or salt thereof.

In some embodiments, the liquid medicament further comprises a second therapeutic agent. Glycosaminoglycans such as heparin are capable of increasing the delivery of a therapeutic agent [12]. In other words, the same molar amount of therapeutic agent administered results in a higher concentration of the agent being delivered to the target site when the glycosaminoglycan is also present. In effect the bioavailability of the second therapeutic agent at the target cells in the lung and/or its airways is increased. Without wishing to be bound by any particular theory, it is believed that the glycosaminoglycan reduces the barrier function of the sputum of the lung and its airways and hence allows the second therapeutic agent to reach the target cells in the airway more easily.

The amount of the drug passing through the mucus, or at the target cells, may be elevated by one, two, three, ten, twenty or more fold by the addition of the glycosaminoglycan. The increase of the amount of the drug reaching the target cells or in the mucus next to the target site may typically be from 5% to 500%, preferably from 50 to 250%, and still more preferably from 50 to 100%.

The target for delivery of the second therapeutic agent may be any part of the respiratory tract including the nasal mucosal membranes. In some embodiments of the invention, the target cells may be present in other parts of the body and the second therapeutic agent passes via the respiratory tract or nasal mucosal membranes to the blood and then onto the target cells. In such embodiments, any of the levels of increase or the amount of agent available, or present, specified herein may be seen in the blood stream and/or at, or in the vicinity of, the target cells. In some embodiments the aim may be to deliver the agent to the whole body or a specific organ, such as for example the brain.

The presence of glycosaminoglycan may effectively increase bioavailability of the second therapeutic agent by at least one fold, two fold, three fold, five fold, ten fold, twenty fold or more. Typically, the presence of glycosaminoglycan may effectively reduce the molar amount or amount by weight of the second therapeutic agent necessary to achieve the same effect in the absence of the glycosaminoglycan by at least a half, a quarter, a fifth, a tenth, or more. Thus the amount of therapeutic agent which has to be administered to achieve the same measurable effect may be decreased, for example by any of these factors or by more than 10%, preferably by more than 20%, more preferably by more than 40%, even more preferably by more than 60%. The amount necessary may be reduced by a factor of one, two, three, five, fifty, one hundred or more fold.

In some embodiments, the second therapeutic agent is an agent useful in the treatment of a respiratory disease. Alternatively, it may be an agent administered to a healthy subject such as, for example, a contraceptive or a smoking suppressant. The agent may be one designed to reduce, eliminate, prevent worsening or prevent development of a symptom of one of the symptoms of a disorder, such as, for example, a symptom of any of the diseases mentioned herein.

The second therapeutic agent may be selected from the group consisting of a bronchodilator, a mucolytic, a mucokinetic, an anti-inflammatory, a protease inhibitor, $\alpha_1$-antitrypsin, a mucoregulator, an anti-pathogenic agent, a gene therapy vector, an antioxidant, a steroid, a corticosteroid, an opioid and a combination of two or more thereof. Examples of possible bronchodilators include salbutamol, salmeterol, tiotropium bromide, glycopyrronium bromide, terbutaline sulfate, and eformoterol. A bronchodilator is preferably a $\beta_2$ agonist, such as salmeterol or indacaterol, or an $M_3$ antagonist, such as tiotropium bromide or glycopyrronium bromide. Examples of anti-inflammatories include an $LTD_4$ antagonist, an $LTB_4$ antagonist, a 5'-lipoxygenase inhibitor, a chemokine inhibitor, a $TNF\alpha$ inhibitor, a soluble TNF receptor and a TNF convertase inhibitor, a prostanoid inhibitor, a thromboxane antagonist and an isoprostane receptor antagonist, a phosphodiesterase-4-inhibitor, an NF-kB inhibitor, an adhesion molecule inhibitor, a p38 MAP kinase inhibitor, and a selective $EP_2$ agonist. Preferred steroids include budesonide and fluticasone. The anti-pathogenic agent may preferably be an antibiotic (such as colistin), an antiviral agent (such as relenza), an antiretroviral agent (such as the HAART—highly active antiretroviral therapy—group of drugs), or an antifungal agent (such as fluconazole or itraconazole). The protease inhibitor may preferably be an inhibitor of elastase, a cathepsin, a matrix metalloproteinase (MMP), an $\alpha_1$-antitrypsin or a serum protease. Gene delivery vectors include viral gene delivery vectors and, for example, gene delivery by adenovirus and adeno-associated virus. The vectors may include genes therapeutic for the conditions mentioned herein such as, for example, the CFTR gene or the $\alpha_1$-antitrypsin gene. In some preferred embodiments, the second therapeutic agent is a bronchodilator, a corticosteroid, or a combination thereof. In other embodiments, the second therapeutic agent is not a bronchodilator. In still further embodiments, the second therapeutic agent is not a corticosteroid.

For a particular therapeutic agent methods will be known to assess their efficacy and the effect they are having. The present invention envisages that such methods can be used, for a specific therapeutic agent, to determine an appropriate quantity, dose and/or concentration of that therapeutic agent to include in the liquid medicament that comprises part of the invention. In a particular embodiment, the second therapeutic agent is a bronchodilator and the nominal dose of bronchodilator provided to the patient is up to 10 mg, preferably up to 5 mg, or up to 2.5 mg, or up to 1 mg, or up to 500 µg, or up to 100 µg, or up to 50 µg. In another embodiment, the second therapeutic agent is a corticosteroid and the nominal dose of corticosteroid provided to the patient is up to 5 mg, preferably up to 2 mg, up to 1 mg, or up to 500 µg.

The ratio of glycosaminoglycan to therapeutic agent present in the liquid medicament is typically a ratio that enables a synergistic effect between the glycosaminoglycan and the therapeutic agent. Thus the amount of glycosaminoglycan used may typically be the amount necessary to reduce the amount of agent which has to be administered to achieve a given effect. The ratio of the therapeutic agent to glycosaminoglycan by weight or alternatively by units may, for example, be from 1:50,000 to 1,000:1, preferably from 1:10,000 to 100:1, more preferably from 1:5,000 to 50:1, and still more preferably be from 1:1,000 to 25:1. The ratio may, for example, be from 1:500 to 1:20, preferably from 1:150 to 1:5, more preferably from 1:50 to 1:2 and even more preferably from 1:10 to 1:1. The therapeutic agent and glycosaminoglycan may, for example, be present in the liquid medicament in equal amounts, or the therapeutic agent may be present in two fold, five fold, ten fold or more than ten fold excess, or the glycosaminoglycan may be present in two fold, five fold, ten fold or more than ten fold excess.

In another embodiment, the liquid medicament further comprises a DNase. Glycosaminoglycans such as heparin are capable of increasing the activity of a DNase and in particular DNase I [13]. The glycosaminoglycan itself does not cleave DNA; rather, it increases the ability of DNase to do so. This synergistic effect means that less DNase is necessary to achieve the same effect and also that higher levels of total activity may be achievable in a system using the same amount of DNase.

The rate of DNA digestion, i.e. the amount of DNA digested per unit time may be increased by one, two, three, ten, twenty or more fold by the addition of the glycosaminoglycan. The enhancement in the DNase activity may typically be from 5% to 5000%, preferably from 50 to 2500%, and more preferably from 75 to 1000%, still more preferably from 100 to 1000%, yet more preferably from 250 to 1000% and even more preferably from 500 to 1000%. These enhancements will typically refer to the amount of DNA the DNase can degrade in a given time and preferably to the activity of the enzyme as expressed in Kunitz units or alternatively Dornase units. One Kunitz unit of DNase will produce a delta A260 of 0.001 per minute per mL at pH 5.0 at 25° C., using DNA as substrate, with [Mg$^{2+}$]=4.2 mM. Preferably the DNA used to assess the DNase activity will be calf thymus or salmon sperm genomic DNA. A Dornase unit is defined as the amount of an enzyme that will cause a decrease of 1.0 relative viscosity unit in a solution of highly polymerised DNA from the original viscosity of 4.0 in 10 minutes at 37° C.

The presence of glycosaminoglycan may effectively increase the number of units of DNase enzyme activity present by at least one fold, two fold, three fold, five fold, ten fold, twenty fold or more. Typically, the presence of glycosaminoglycan may effectively reduce the molar amount of DNase necessary to achieve the same activity in the absence of the glycosaminoglycan by at least a half, a quarter, a fifth, a tenth, or more. The glycosaminoglycan may ensure a more complete digestion of DNA in a given time by the same amount of DNase; thus the average, or main, fragment size, present may typically be two, three, five, ten, twenty, fifty or more than fifty times longer in the absence than in the presence of glycosaminoglycan following incubation for an equivalent amount of time.

Preferably, the DNase will be a DNase I. However, in some embodiments it may be a DNase II. DNases occur in a number of species and any DNase capable of cleaving DNA may be present in the liquid medicament. The DNase may be from an animal source such as of bovine or porcine origin. It may be of plant, fungal, or microbial origin. However, typically and most preferably the DNase is of human origin and is preferably a recombinant human DNase. Commercially available DNase preparations such as Dornase™ and Pulmozyme™ may be used in the liquid medicament. The DNase will have hydrolytic activity, e.g. in the case of DNase I it may hydrolyse DNA to give 5'-phosphate nucleotides and in the case of DNase II it may hydrolyse DNA to give 3'-phosphate nucleotides. Hydrolytic activity may be assessed in a variety of ways known in the art such as analytical polyacrylamide and agarose gel electrophoresis, hyperchromicity assay [14], or methyl green assay [15].

The DNase will preferably display mucolytic activity for samples of mucus containing DNA. Mucolytic activity refers to the reduction of viscoelasticity (viscosity) of mucus. Mucolytic activity may be determined by any of several different methods known in the art, including sputum compaction assay [16], assays using a torsion pendulum [17], or other suitable rheological methodologies.

A number of methods are known for assaying for DNase activity, such as the fluorescence-based assay of Labarce & Paiden using Hoechst Stain [18]. The present invention envisages that such methods can be used to determine an appropriate quantity or units of DNase to include in the liquid medicament that comprises part of the vibrating mesh nebuliser.

The ratio of glycosaminoglycan to DNase present in the liquid medicament is typically a ratio that enables a synergistic effect between the glycosaminoglycan and DNase activity. Thus one or more of the values given herein for an increase in DNase activity may be achieved. The ratio of DNase to glycosaminoglycan by weight or alternatively by units may, for example, be from 1:50,000 to 1,000:1, preferably from 1:10,000 to 100:1, more preferably from 1:5,000 to 50:1, and still more preferably be from 1:1,000 to 25:1. The ratio may, for example, be from 1:500 to 1:20, preferably from 1:150 to 1:5, more preferably from 1:50 to 1:2 and even more preferably from 1:10 to 1:1. The DNase and glycosaminoglycan may, for example, be present in the liquid medicament in equal amounts, or the DNase may be present in two fold, five fold, ten fold or more than ten fold excess, or the glycosaminoglycan may be present in two fold, five fold, ten fold or more than ten fold excess.

In another embodiment, the liquid medicament further comprises a non-therapeutic agent. Non-therapeutic agents include, but are not limited to, contraceptives and labelling agents, such as a radioactive, fluorescent or other labelled molecule. In some cases, a particular molecule may have both a therapeutic and a non-therapeutic utility.

The liquid medicament for use in accordance with the present invention may include, in addition to one or more of the components described above, a pharmaceutically acceptable excipient, carrier, buffer, diluent, stabiliser, humectant, surfactant or other materials well known to those skilled in the art. In particular they may include a pharmaceutically acceptable excipient. Such materials should be non-toxic and should not interfere with the efficacy of any active ingredient in the medicament.

The following are Examples that illustrate the invention. However, these Examples are in no way intended to limit the scope of the invention.

EXAMPLES

The data presented below was collected according to international standards and guidelines. Among various cascade impactors, the next-generation impactor (NGI) is the apparatus recommended by the USP and ERS guidelines [19] for the assessment of aerodynamic droplet sizes from nebuliser systems, because it is a direct measurement of drug mass deposited based on aerodynamic droplet sizes. Alternatively, laser diffractometry is accepted for droplet size measurement specifically for homogeneous solutions, but not for dispersed systems or when significant droplet evaporation occurs. The test should be performed at airflow rate of 15 L/min and with a cooled impactor to avoid droplet evaporation. The seven stages of the NGI therefore present the following cut-off diameters: 0.98, 1.36, 2.08, 3.30, 5.39, 8.61, and 14.1 μm. Besides the microorifice collector (MOC) plate, an external filter is also recommended to collect very small droplets [summarised in 1].

Example 1: Nebulisation of Aqueous Heparin Solutions Using the PARI eFlow®

Physicochemical characterisation was carried out on three concentrations of aqueous heparin solutions, and the results are displayed in Table 1. Tests for viscosity, surface tension and osmolality were carried out in triplicate. For pH and density single measurements were performed.

TABLE 1

Results of physicochemical characterization for solutions of heparin in water.

| | 6 mg/mL | | 30 mg/mL | | 150 mg/mL | |
|---|---|---|---|---|---|---|
| Concentration | Mean | SD | Mean | SD | Mean | SD |
| viscosity [mPa · s] | 1.25 | 0.01 | 1.99 | 0.02 | 8.90 | 0.08 |
| surface tension [mN/m] | 72.58 | 0.14 | 72.41 | 0.02 | 73.78 | 0.05 |
| osmolality [osmol/kg] | 0.014 | 0.001 | 0.056 | 0.001 | 0.293 | 0.001 |

TABLE 1-continued Results of physicochemical characterization for solutions of heparin in water.

| | 6 mg/mL | | 30 mg/mL | | 150 mg/mL | |
|---|---|---|---|---|---|---|
| Concentration | Mean | SD | Mean | SD | Mean | SD |
| pH | 6.50 | N/A | 6.01 | N/A | 5.97 | N/A |
| density [g/cm$^3$] | 1.00 | N/A | 1.01 | N/A | 1.07 | N/A |

SD = standard deviation.
N/A = not applicable.

These results show that the dynamic viscosity of the heparin solution increases with concentration. There is a moderate increase from 1.25±0.01 to 1.99±0.02 mPa·s between 6 and 30 mg/mL and a strong increase to 8.9±0.08 mPa·s when the concentration is further increased to 150 mg/mL. The surface tension (nearly equal to that of water) remains constant between 6 and 30 mg/mL and increases only slightly (from 72.41±0.02 to 73.78±0.05 mN/m) between 30 and 150 mg/mL. As expected the osmolality increases with increasing concentration, going from 0.014±0.001 to 0.293±0.001 osmol/kg over the investigated concentration range. There is a small increase in density with concentration (1.00 to 1.07 g/cm$^3$). All formulations show a pH (between 5.97 and 6.50) which would be appropriate for inhalation (the allowed range according to the European Pharmacopoeia is pH 3.0-8.5). The heparin solutions were nebulised using a PARI eFlow® device configured with Head class 40, which typically results in droplet sizes from 4.0-4.9 µm when using dilute aqueous formulations. The properties of the resultant aerosol particles were measured using laser diffraction, and are compared with the results obtained for isotonic saline measured using the same nebuliser configuration in Table 2.

TABLE 2

Results of laser diffraction for nebulised saline and heparin solutions.

| | Saline | | 6 mg/mL heparin | | 30 mg/mL heparin | | 150 mg/mL heparin |
|---|---|---|---|---|---|---|---|
| Solution | Mean | SD | Mean | SD | Mean | SD | Mean |
| MMD [µm] | 4.7 | 0.2 | 4.6 | 0.1 | 4.4 | 0.1 | n.d. |
| GSD | 1.62 | 0.07 | 1.52 | 0.01 | 1.52 | 0.01 | n.d. |
| RF [% <5 µm] | 56.3 | 4.5 | 57.9 | 2.7 | 63.0 | 3.3 | n.d. |
| TOR [mg/min] | 976 | 191 | 805 | 55 | 623 | 69 | <50 |

MMD = median mass diameter;
GSD = geometric standard deviation;
RF = respirable fraction;
TOR = total output rate;
SD = standard deviation;
n.d. = not determined.

It was found that the heparin formulations of 6 and 30 mg/mL concentration could be nebulised well. The 150 mg/mL formulation could not be nebulised with sufficient output rate (<50 mg/min) to allow for the droplet size distribution to be measured.

Comparing the droplet sizes of the nebulized heparin formulations with pure saline, it can be seen that the MMD decreases slightly with increasing heparin concentration (from 4.7 µm for saline to 4.4 µm for 30 mg/mL heparin). This corresponds to a slight increase in respirable fraction (RF, droplets <5 µm) from around 56% to 63%. The Total Output Rate (TOR) decreases with increasing concentration but is still high enough at 30 mg/mL (623±69 mg/mL) to leave room for further optimization.

These data therefore demonstrate that nebulisation of heparin solutions with nebulisers based on eFlow® technology is possible. Heparin formulations of 6 and 30 mg/mL were aerosolised well.

Example 2: Nebulisation of Aqueous Heparin Solutions Using the Aeroneb® Go

Particle Size Distribution

The particle size distribution of heparin solutions was measured after aerosolisation of the heparin solutions using the Aeroneb® Go nebuliser. Particle size measurements were made using the HELOS KR particle sizer device, INHALER module, and WINDOX 5.0 software from SympatecGmbH (Clausthal-Zellerfeld, Germany). The total volume of solution in the reservoir of the nebuliser was 6 mL: 1.5 mL heparin (Wokhardt, 25,000 IU/mL) with 4.5 mL 0.9% aqueous NaCl (final concentration of heparin=6250 IU/mL or 31.25 mg/mL; final concentration of NaCl=154 mM). The viscosity of the solution was 1.7 mPa·s. The nebulisation time was 14 min (reservoir empty); particle size measurements were divided into 1 min intervals. The results are shown in FIG. 1. The particle distribution is seen to be bimodal. The X50 is 3.45±0.025 m (mean±standard deviation), where 50% of the total number of the particles is in particles less than this size. The X90 shows that 90% of the particles have a diameter less than 8.5 m. 57.87%±0.35% of particles were observed to fall within the respirable range of 1-5 µm. Optical concentration (droplets in laser pathway) was used as an indication of nebulisation efficiency; this nebulisation efficiency was determined to be 76.91%±4.25%.

Cascade Impaction Data

Subsequently cascade impaction data was collected for the nebulised heparin solutions using the NGI (Next Generation Impactor). Again, an Aeroneb® Go device was filled with 6 mL of solution: 1.5 mL heparin (Wokhardt, 25,000 IU/mL) with 4.5 mL 0.9% aqueous NaCl (final concentration of heparin=6,250 IU/mL or 31.25 mg/mL; final concentration of NaCl=154 mM). The solution was delivered to the NGI at a flow rate of 15 L/min to model inspiratory flow. Heparin was collected from the stages and analysed using UV analysis in water against a heparin standard concentration curve. The data is shown in Table 3. Ideal deposition occurs at stages 3 to 6, representing central and peripheral airways. The data shows that 48% of the loading dose is potentially deposited in the airways.

TABLE 3

Cascade impaction data for nebulised heparin solutions from an Aeroneb ® Go device.

| | % Deposition | | | Average % |
|---|---|---|---|---|
| | Test 1 | Test 2 | Test 3 | (SD) |
| Induction port | 2.74 | 1.65 | 1.08 | 1.82 (0.84) |
| Stage 1 | 7.43 | 7.82 | 4.21 | 6.49 (1.99) |
| Stage 2 | 5.08 | 9.74 | 4.33 | 6.38 (2.93) |
| Stage 3 | 7.15 | 16.84 | 7.58 | 10.52 (5.48) |
| Stage 4 | 11.86 | 25.39 | 12.12 | 16.46 (7.74) |
| Stage 5 | 10.79 | 21.39 | 10.34 | 14.17 (6.25) |
| Stage 6 | 5.28 | 10.95 | 4.46 | 6.89 (3.53) |
| Stage 7 | 2.40 | 5.32 | 1.08 | 2.93 (2.17) |
| Micro-Orifice Collector (MOC) | 2.59 | 1.09 | 1.20 | 1.63 (0.84) |
| % from induction port to MOC | 55.33 | 100.19 | 46.39 | 67.31 (2.45) |

Variation in Salt Concentration

Aqueous solutions of unfractionated heparin as its sodium salt containing various concentrations of an added inorganic salt were also aerosolised using the Aeroneb® Go. Particle size measurements were made using the HELOS KR particle sizer device, INHALER module, and WINDOX 5.0 software from SympatecGmbH (Clausthal-Zellerfeld, Germany). The heparin sodium salt was obtained from pig intestinal mucosa (Calbiochem, molecular weight 12-15 kDa, 192 U/mg). The particle size distributions are shown in FIGS. 2-7 and the important parameters, quoted as mean values ±standard deviations, are summarised in Table 4 below. Viscosity measurements were conducted in triplicate using the BS/U-tube viscometer, size number B, nom. constant 0.01, and are presented as the mean value, The pH of all the salt solutions tested was in the range of 6.5-7.0 and the particle size distributions were observed to be bimodal.

Salt was added to 40 mg/mL heparin solutions in a range of NaCl concentrations from 140 mM NaCl to 224 mM NaCl. Generally, an increase in the salt concentration caused a decrease in the viscosity of the solution. Without wishing to be bound by any particular theory, it is believed that an increase in the salt concentration causes the polymer to coil. The decrease in viscosity was dependent on charge rather than the number of ions, as 40 mg/mL heparin in 112 mM NaCl plus 56 mM $MgCl_2$ had the same viscosity as heparin in 224 mM NaCl (i.e. 2 mPa·s).

At all viscosities, a 40 mg/mL solution of heparin in solution with a range of NaCl concentrations was nebulised using the Aeroneb Go with a respirable fraction between 1 and 5 μM of 50.76%, 56.65%, 48.62%, 55%, 57.02% and 58.46% for 40 mg/mL heparin solutions with viscosities of 2.22, 2.25, 2.2, 2.2, 2 and 2 mPa·s respectively.

Example 3: Nebulisation of Aqueous Heparin Solutions in the Aeroneb® Go in the Absence and Presence of a Second Therapeutic Agent A 40 mg/mL aqueous solution of heparin containing 140 mM NaCl was aerosolised using the Aeroneb® Go nebuliser in the absence and presence of salbutamol (a bronchodilator) and dexamethasone (a corticosteroid). Particle size measurements were made using the HELOS KR particle sizer device, INHALER module, and WINDOX 5.0 software from SympatecGmbH (Clausthal-Zellerfeld, Germany).

Nebulisation of Heparin in the Absence of a Second Therapeutic Agent

Figure 8:
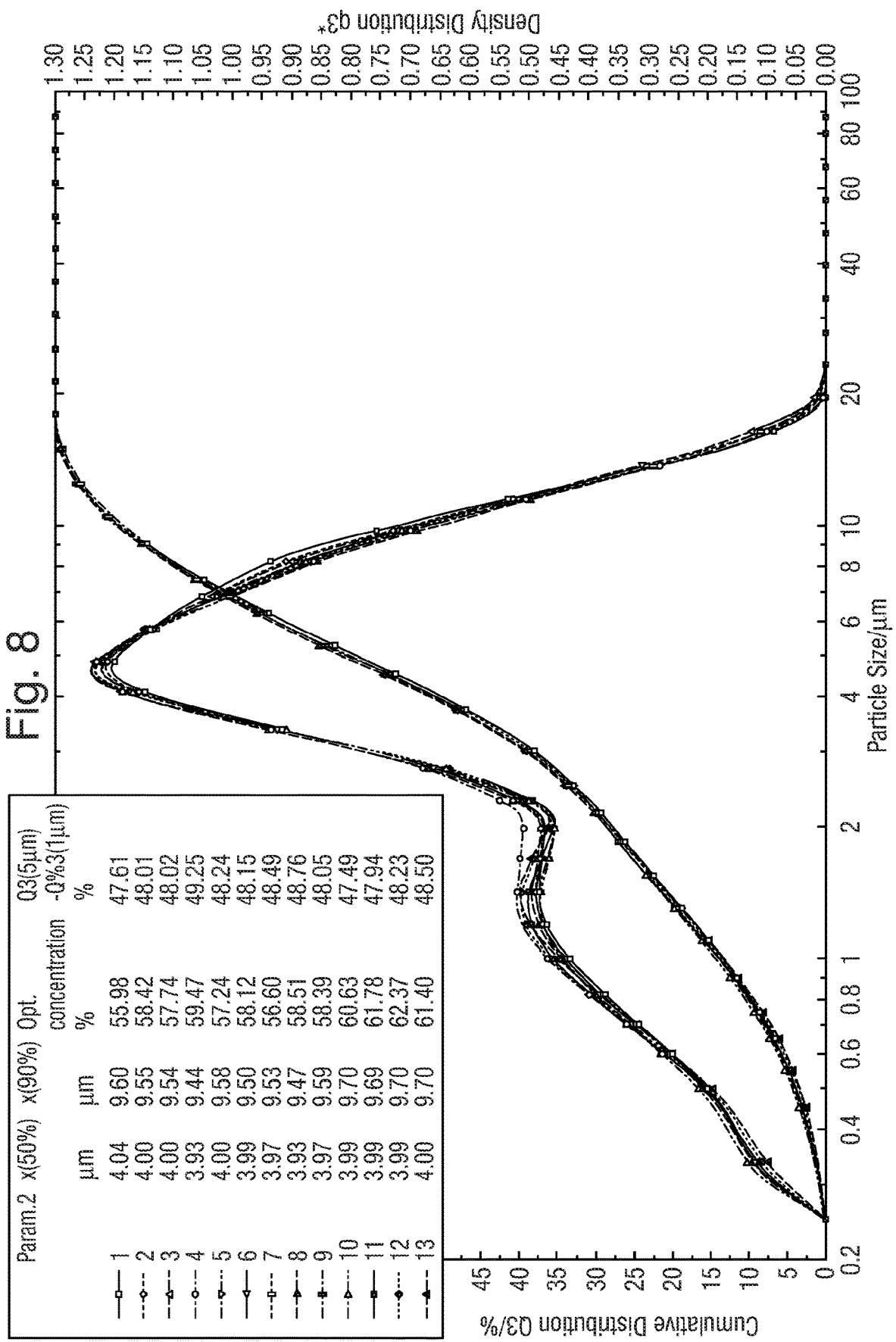
FIG. 8: Frequency density distribution and cumulative frequency distribution of particle size observed when aqueous solutions containing 40 mg/mL heparin and 140 mM NaCl are nebulised in the Aeroneb® Go.

The total volume of solution in the reservoir of the nebuliser was 6 mL unfractionated heparin (final concentration 40 mg/mL; viscosity 2.2 mPa·s) with aqueous NaCl (final concentration 140 mM). The nebulisation time was 12 min (reservoir empty); particle size measurements were divided into 1 min intervals. The results are shown in FIG. 8. The particle distribution is seen to be bimodal, with a

TABLE 4

Particle size data for nebulised heparin solutions containing an added inorganic salt from an Aeroneb ® Go device.

| Heparin concentration (mg/mL) | Inorganic salt concentration (mM) | | Viscosity (mPa · s) | VMD (μm) | X50 (μm) | Particles in 1-5 μm range (%) | Optical concentration (%) |
|---|---|---|---|---|---|---|---|
| | NaCl | $MgCl_2$ | | | | | |
| 40 | 0 | 0 | 2.5 | n.d. | n.d. | n.d. | n.d. |
| 40 | 140 | 0 | 2.22 | 4.80 ± 0.06 | 4.095 ± 0.044 | 50.76 ± 0.63 | 60.79 ± 1.75 |
| 40 | 168 | 0 | 2.25 | 4.41 ± 0.025 | 3.543 ± 0.049 | 56.65 ± 0.47 | 72.97 ± 2.92 |
| 40 | 196 | 0 | 2.2 | 4.68 ± 0.02 | 3.978 ± 0.022 | 48.62 ± 0.38 | 49.3 ± 2.87 |
| 40 | 210 | 0 | 2.2 | 4.55 ± 0.023 | 3.812 ± 0.027 | 55 ± 0.24 | 52.92 ± 2.73 |
| 40 | 224 | 0 | 2.0 | 4.37 ± 0.032 | 3.51 ± 0.03 | 57.02 ± 0.28 | 74.14 ± 1.98 |
| 40 | 112 | 56 | 2.0 | 4.31 ± 0.05 | 3.49 ± 0.056 | 58.46 ± 0.30 | 59.66 ± 2.49 |

VMD = volume median diameter;
n.d. = not determined.

A 40 mg/mL solution of aqueous heparin in the absence of inorganic salt was not nebulised; this was not due to its viscosity, but rather due to the lack of salt in the solution. The addition of salt to improve nebulisation is a known feature of the Aeroneb® Go device, and has previously been reported for mannitol solutions. The viscosity of heparin in solution also depends on ionic strength. Heparin is thought to be a rigid rod in aqueous solutions in water and a random coil that condenses in salt solutions, which are therefore less viscous than those in water [20].

VMD of 4.64±0.033 μm and an X50 of 3.98±0.03 m. 48.21%±0.46% of particles were observed to fall within the respirable range of 1-5 μm. Optical concentration (droplets in laser pathway) was used as an indication of nebulisation efficiency; this nebulisation efficiency was determined to be 58.97% 2.021%.

Nebulisation of Heparin in the Presence of Salbutamol

Figure 9:
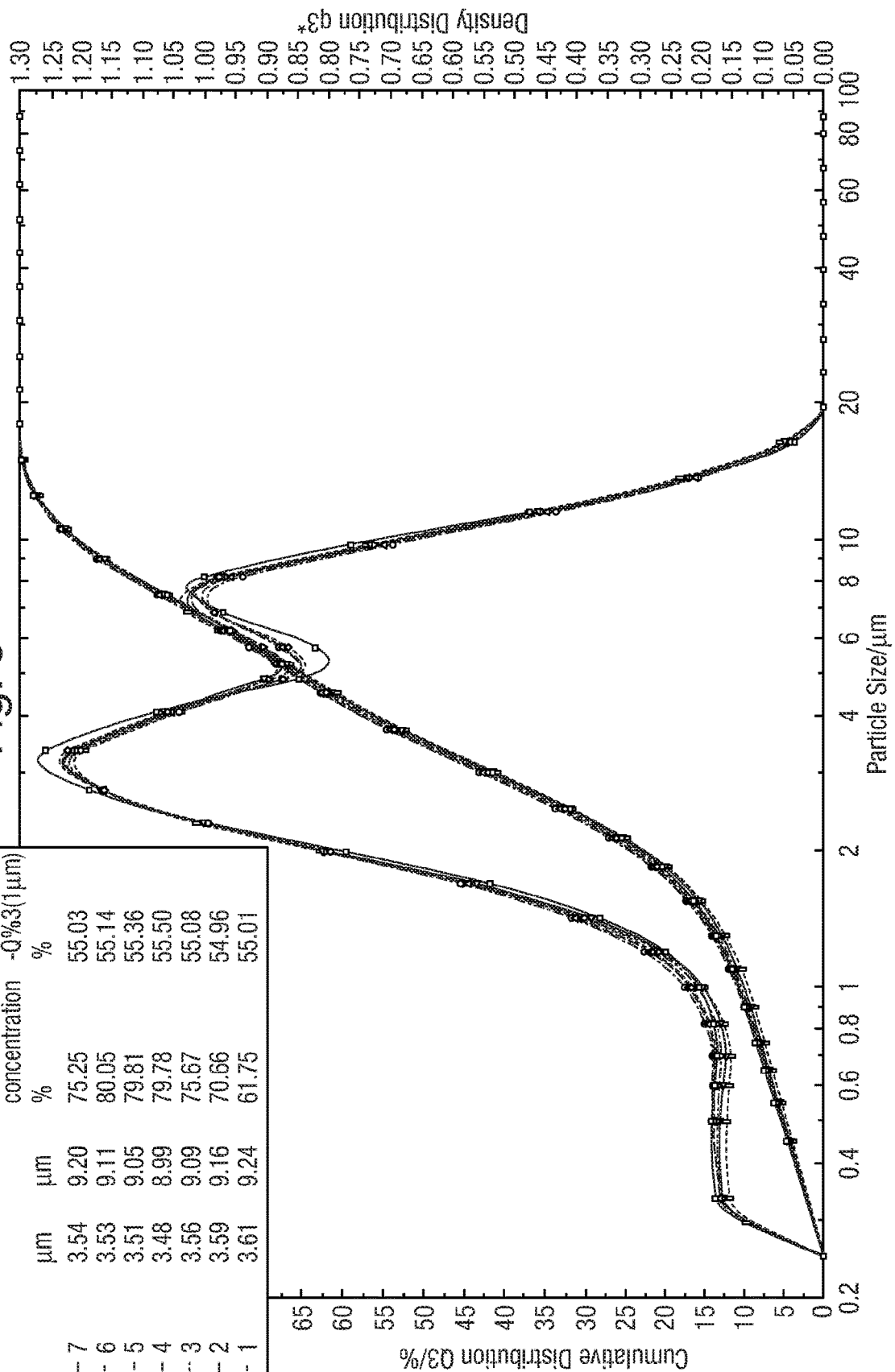
FIG. 9: Frequency density distribution and cumulative frequency distribution of particle size observed when aqueous solutions containing 40 mg/mL heparin, 140 mM NaCl and 0.83 mg/mL salbutamol are nebulised in the Aeroneb® Go.

The total volume of solution in the reservoir of the nebuliser was 3 mL. The final concentration of unfractionated heparin was 40 mg/mL, the final concentration of NaCl was 140 mM and the final concentration of salbutamol was 0.83 mg/mL. The nebulisation time was 7 min (3 mL nebulised); particle size measurements were divided into 1 min intervals. The results are shown in FIG. 9. The particle distribution is seen to be bimodal, with a VMD of 4.47±0.054 m and an X50 of 3.546±0.045 μm. 55.154%±0.20% of particles were observed to fall within the respirable range of 1-5 m. Optical concentration (droplets in laser pathway) was used as an indication of nebulisation efficiency; this nebulisation efficiency was determined to be 76.87%±3.738%.

Nebulisation of Heparin in the Presence of Dexamethasone

Figure 10:
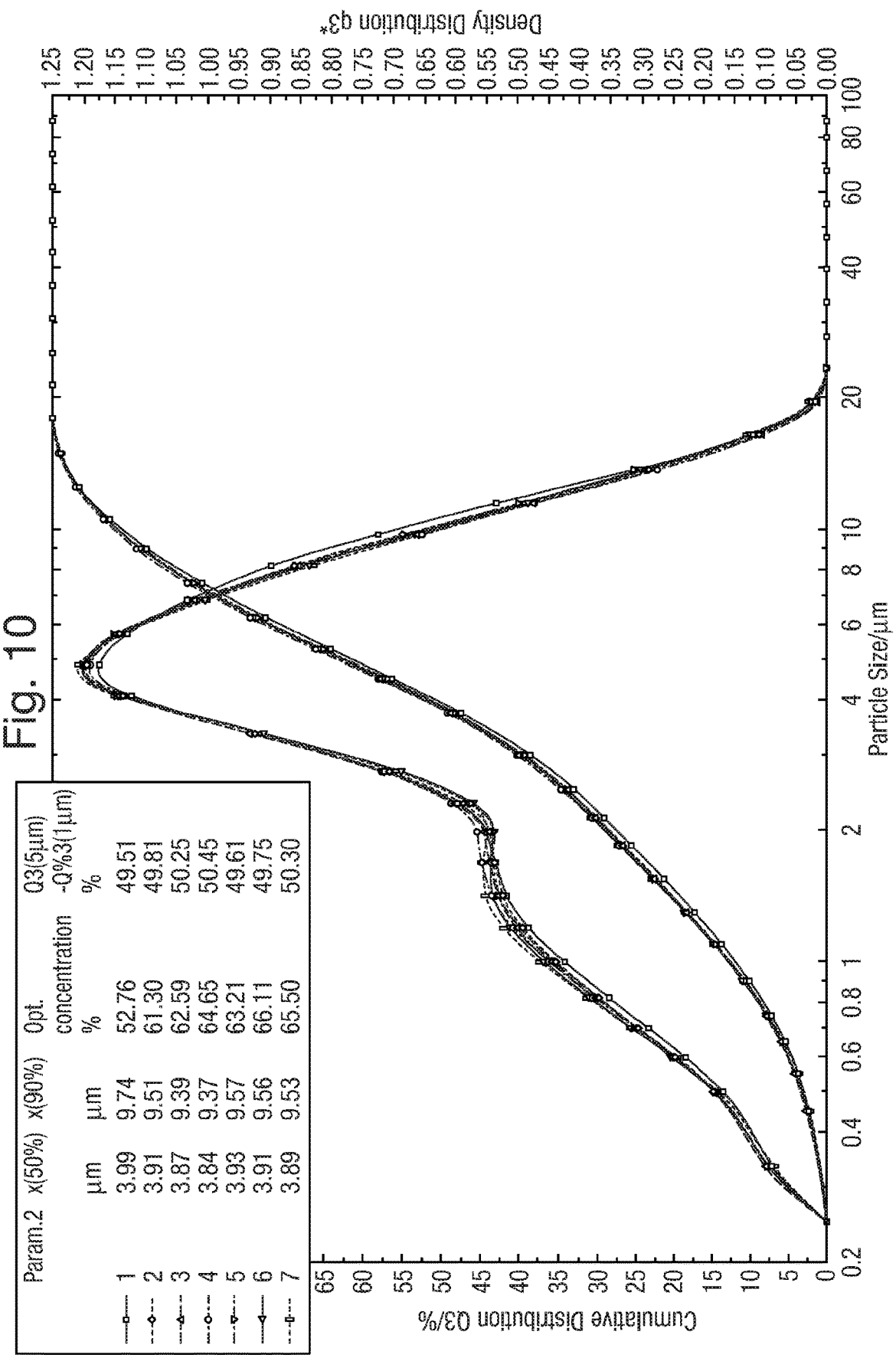
FIG. 10: Frequency density distribution and cumulative frequency distribution of particle size observed when aqueous solutions containing 40 mg/mL heparin, 140 mM NaCl and 0.75 mg/mL dexamethasone are nebulised in the Aeroneb® Go.

The total volume of solution in the reservoir of the nebuliser was 3 mL. The final concentration of unfractionated heparin was 40 mg/mL, the final concentration of NaCl was 140 mM and the final concentration of dexamethasone was 0.75 mg/mL. The nebulisation time was 7 min (3 mL nebulised); particle size measurements were divided into 1 min intervals. The results are shown in FIG. 10. The particle distribution is seen to be bimodal, with a VMD of 4.61±0.058 m and an X50 of 3.906±0.048 μm. 49.954%±0.372% of particles were observed to fall within the respirable range of 1-5 m. Optical concentration (droplets in laser pathway) was used as an indication of nebulisation efficiency; this nebulisation efficiency was determined to be 62.303%±4.53%.

CONCLUSIONS

Heparin (40 mg/mL in 140 mM NaCl) alone and in combination with either salbutamol or dexamethasone, was nebulised successfully from the Aeroneb® Go. Unexpectedly, the presence of salbutamol improved the particle size profile. Significantly, a large respirable fraction of particles between 1-5 μm was observed, as was an increased nebulisation efficiency (optical concentration); the presence of salbutamol also reduced both the X50 (from 3.98±0.03 μm to 3.546±0.045 μm) and the VMD (from 4.64±0.033 μm to 4.47+0.054 μm). Similar, but smaller trends were seen in the presence of dexamethasone. Unexpectedly, the presence of heparin enhanced the solubility of dexamethasone, which was not soluble at 0.25 mg/mL in 140 mM NaCl alone, but was soluble in a solution of 140 mM NaCl containing 40 mg/mL heparin.

Figure 11:
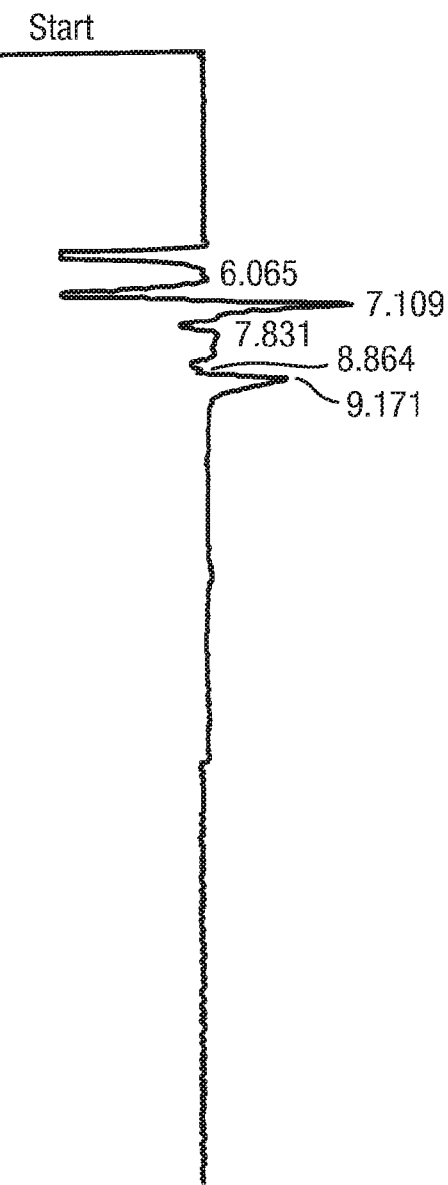
FIG. 11: High performance liquid chromatography (HPLC) traces for unfractionated heparin (0.25 mg/mL in water) before (left) and after (right) nebulisation using the Pari eFlow®.
Figure 11:
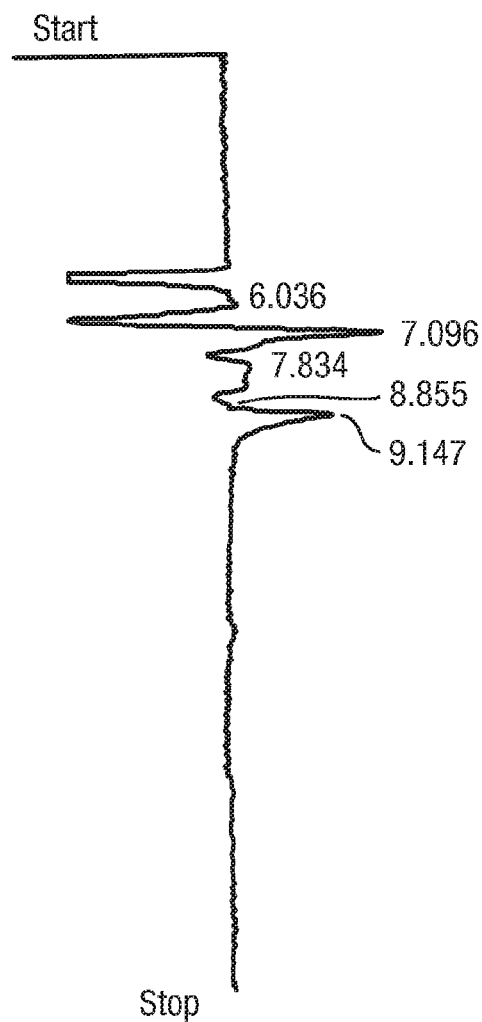

Example 4: Analysis of Samples of Unfractionated Heparin by HPLC Before and After Nebulisation A solution of unfractionated heparin (diluted to 50 U/mL, i.e. 0.25 mg/mL, in ultra high quality water) was analysed by high performance liquid chromatography. HPLC analysis was performed using a 5 m ion-paring C8 column (Hichrom, Reading, UK), a Rheodyne 7725 syringe loading sample injector fitted with a 20 μL loop (Rheodyne, Cotati, CA, USA), a LKB2150 dual piston pump (LK Bromma, Swedon), a HP 1050CVW detector (Agilent, UK), a HP 3396A integrator (Agilent, UK) and a Rheodyne 25 μL capacity syringe was used to load a 20 μL sample into the injection port. HPLC conditions consisted of an ultraviolet wavelength selected at 232 nm. The flow rate was adjusted to 0.50 mL/min and a pressure of 50 bar was recorded. A mobile phase composed of 30% acetonitrile and 70% aqueous solution comprising 15 mM tetrabutylammonium hydroxide and 50 mM ammonium acetate in HPLC grade water, adjusted to pH 7 with acetic acid, was used. The resulting HPLC trace is shown as the left-hand trace in FIG. 11.

An identical sample of unfractionated heparin was nebulised using the PARI eFlow® device, and recollected. This nebulised sample was analysed under identical HPLC conditions as sample that was not nebulised. The resulting HPLC trace is shown as the right-hand trace in FIG. 11.

The very high similarity between these two HPLC traces indicates that nebulisation has no effect on the structural integrity of the unfractionated heparin molecules. It is therefore clear that nebulisation of the unfractionated heparin does not lead to degradation. This is a surprising result, given that vibrating mesh nebulisers are considered in the art to be unsuitable for delivery of other flexible polymers, such as non-complexed DNA, due to high levels of degradation observed during nebulisation. It was considered that flexible polymers were easily distorted, degraded and inactivated when subjected to fluid flow.

In an additional experiment, it was also observed that the anti-coagulant activity of the unfractionated heparin was retained after nebulisation from the PARI eFlow® device.

REFERENCES

The contents of each of the following references are incorporated herein in their entirety:

[1] Carvalho T C, McConville J T. The function and performance of aqueous aerosol devices for inhalation therapy. J Pharm Pharmacol 2016.

[2] Ari A. Jet, ultrasonic, and mesh nebulizers: an evaluation of nebulizers for better clinical outcomes. Eurasian J Pulmonol 2014; 16: 1-7.

[3] Practical Pharmaceutics: An International Guideline for the Preparation Care and Use of Medicinal Products. Springer, 2009, eds. Bouwman Y, Fenton-May V, Le Brun P.

[4] Ghazanfari T, Elhissi A M A, Ding Z, Taylor K M G. The influence of fluid physiocochemical properties on vibrating-mesh nebulization. Int J Pharm 2007; 339: 103-111.

[5] Shute J K, Carroll M P, Conway H J, Hockey P M. Use of glycosaminoglycans such as e.g. heparin for the treatment of respiratory disorders such as COPD. WO 03/068187.

[6] Ehrlich J, Stivala S S. Chemistry and pharmacology of heparin. J Pharm Sci 1973; 62: 517-545.

[7] Guo X, Condra M, Kimura K, Berth G, Dautzenberg H, Dubin P L. Determination of molecular weight of heparin by size exclusion chromatography with universal calibration. Anal Biochem 2003; 312: 33-39.

[8] Bendstrup K E, Newhouse M T, Pedersen O F, Jensen J I. Characterization of heparin aerosols generated in jet and ultrasonic nebulizers. J Aerosol Med 1999; 12: 17-25.

[9] Lenney W, Edenborough F, Kho P, Kovarik J M. Lung deposition of inhaled tobramycin with eFlow rapid/LC Plus jet nebuliser in healthy and cystic fibrosis subjects. J Cyst Fibros 2011; 10: 9-14.

[10] http.//www.phillips-allies-summit.com/workshops.html (accessed 28 June 2016).

[11] (a) Quanjer PhH, Tammeling G J, Cotes J E, Pedersen O F, Yernault J-C. Lung volumes and forced ventilatory flows. European Resp. Journal, 1993; 6: Suppl. 16. (b) Coates. Lung Function: Assessment and Applications In Medicine, 4th Edition, Oxford, Blackwell, 1969.

[12] Shute J K, Carroll M P, Conway H J, Hockey P M. Combination therapy for respiratory disorders. WO 03/068188.

[13] Shute J K, Carroll M P, Conway H J, Hockey P M. Glycosaminoglycan-D Nase combination therapy. WO 03/068254.

[14] Kunitz M. Crystalline desoxyribonuclease: I. Isolation and general properties spectrophotometric method for the measurement of desoxyribonucelase activity; and II. Digestion of thymus nucleic acid (desoxyribonucleic acid) the kinetics of the reaction. J Gen Physiol 1950; 33(4): 349-362 and 363-377.

[15] (a) Kurnick. Arch Biochem 1950; 29: 41-54. (b) Sinicropi D, Baker D L, Prince W S, Shiffer K, Shak S. Colorimetric determination of DNase I activity with a DNA-methyl green substrate. Anal Biochem 1994; 222(2): 351-358.

[16] See, for example, WO 94/10567.

[17] Janmey P A. A torsion pendulum for measurement of the viscoelasticity of biopolymers and its application to actin networks. J Biochem Biophys Methods 1991; 22(1): 41-53.

[18] Labarca C, Paigen K. A simple, rapid, and sensitive DNA assay procedure. Anal Biochem 1980; 102(2): 344-352.

[19] Boe J, Dennis J H, O'Driscoll B R. European Respiratory Society Guidelines on the use of Nebulizers. Eur Respir J 2001; 18: 228-242.

[20] Liberti P A, Stivala S S. Physicochemical Studies of Fractionated Bovine Heparin: II. Viscosity as a Function of Ionic Strength. Archives of Biochemistry and Biophysics 1967; 119: 510-518.

The invention claimed is:

1. A method of treating a respiratory disease in a patient, which method comprises administering a liquid medicament to the respiratory system of the patient by a vibrating mesh nebuliser, wherein the vibrating mesh nebuliser comprises:
a housing having a reservoir for the liquid medicament; and
the liquid medicament,
wherein the liquid medicament comprises:
i) an unfractionated heparin or a physiologically acceptable salt thereof or a derivative thereof, wherein the unfractionated heparin or the physiologically acceptable salt thereof or the derivative thereof has an average molecular weight of from >8 to 40 kDa; and
ii) an inorganic salt selected from the group consisting of halides, oxides, hydroxides, sulfates, carbonates, phosphates, nitrates, acetates, and oxamates of lithium, sodium, potassium, magnesium, calcium, aluminium, zinc and ammonium,
wherein the concentration of the unfractionated heparin or the physiologically acceptable salt thereof or the derivative thereof in the liquid medicament is from 15 to 40 mg/mL,
wherein the total concentration of the inorganic salt in the liquid medicament is from 10 to 300 mM, and
wherein the respiratory disease (a) is characterised by mucous hyper secretion or elevated mucous viscosity, or (b) is selected from the group consisting of chronic obstructive pulmonary disease, emphysema, cystic fibrosis, bronchitis, asthma, bronchiectasis, primary ciliary dyskinesia, pneumonia, sinusitis, sinus congestion, influenza, a cold, a viral infection, a bacterial infection, and a fungal infection.

2. The method of claim 1, wherein the method further comprises reducing the viscosity of mucous in the respiratory system of the patient.

3. The method of claim 1, wherein the respiratory disease is chronic obstructive pulmonary disease.

4. The method of claim 1, wherein the respiratory disease is cystic fibrosis.

5. The method of claim 1, wherein the respiratory disease is bronchiectasis.

6. The method of claim 1, wherein the patient to be treated is an ambulatory patient or a patient not requiring mechanical ventilation.

7. The method of claim 1, wherein the unfractionated heparin or the physiologically acceptable salt thereof or the derivative thereof has an average molecular weight of from 12 to 18 kDa.

8. The method of claim 1, wherein:
(a) the inorganic salt is selected from the group consisting of sodium chloride and magnesium chloride; and/or
(b) the total concentration of the inorganic salt in the liquid medicament is from 100 to 200 mM.

9. The method of claim 1, wherein the liquid medicament has a viscosity of from 1.6 mPa·s to 4.0 mPa·s.

10. The method of claim 1, wherein the concentration of unfractionated heparin or the physiologically acceptable salt thereof or the derivative thereof in the liquid medicament is from 25 to 35 mg/mL.

11. The method of claim 1, wherein the unfractionated heparin or the physiologically acceptable salt thereof or the derivative thereof retains anti-coagulant activity.

12. The method of claim 1, wherein the unfractionated heparin or the physiologically acceptable salt thereof or the derivative thereof lacks anti-coagulant activity.

13. The method of claim 3, wherein the patient to be treated:
(a) has an FEV1 which is from 10 to 80%, or from 20 to 50%, of the predicted value for an equivalent patient not suffering from chronic obstructive pulmonary disease; or
(b) has an FEV1 which is greater than 80% of the predicted value for an equivalent patient not suffering from chronic obstructive pulmonary disease.

14. The method of claim 1, wherein the liquid medicament facilitates the clearance of mucus from the central and peripheral airways of the patient.

15. The method of claim 1, wherein the method further comprises administration of a second therapeutic agent and/or DNase to the patient.

16. A method of treating a respiratory disease in a patient, which method comprises administering a liquid medicament to the respiratory system of the patient by a vibrating mesh nebuliser, wherein the vibrating mesh nebuliser comprises:
a housing having a reservoir for the liquid medicament; and
the liquid medicament,
wherein the liquid medicament comprises:
i) an unfractionated heparin or a physiologically acceptable salt thereof or a derivative thereof, wherein the unfractionated heparin or the physiologically acceptable salt thereof or the derivative thereof has an average molecular weight of from >8 to 40 kDa;
ii) an inorganic salt which is selected from the group consisting of halides, oxides, hydroxides, sulfates, carbonates, phosphates, nitrates, acetates, and oxamates of lithium, sodium, potassium, magnesium, calcium, aluminium, zinc and ammonium, and
iii) a second therapeutic agent and/or DNase,
wherein the concentration of the unfractionated heparin or the physiologically acceptable salt thereof or the derivative thereof in the liquid medicament is from 15 to 40 mg/mL, wherein the total concentration of the inorganic salt in the liquid medicament is from 10 to 300 mM, wherein the respiratory disease (a) is characterised by mucous hyper secretion or elevated mucous viscosity, or (b) is selected from the group consisting of chronic obstructive pulmonary disease, emphysema, cystic fibrosis, bronchitis, asthma, bronchiectasis, primary ciliary dyskinesia, pneumonia, sinusitis, sinus congestion, influenza, a cold, a viral infection, a bacterial infection, and a fungal infection, and wherein, when the liquid medicament comprises a second therapeutic agent: (i) both the second therapeutic agent and the unfractionated heparin or the physiologically acceptable salt thereof or the derivative thereof are intended to have a therapeutic effect; or (ii) only the second therapeutic agent is intended to have a therapeutic effect and the unfractionated heparin or the physiologically acceptable salt thereof or the derivative thereof is intended to facilitate delivery of the second therapeutic agent to its target site in the body, optionally wherein the ratio of the amount of the unfractionated heparin or the physiologically acceptable salt thereof or the derivative thereof to the amount of the second therapeutic agent or DNase in the liquid medicament is from 500:1 to 1:500, or from 25:1 to 1:25.

17. The method of claim 15, wherein the second therapeutic agent and/or DNase is delivered to the respiratory system of the patient by a different method of administration to the unfractionated heparin or physiologically acceptable salt thereof or derivative thereof, wherein said method of administration is intranasal or via instillation.

18. The method of claim 15, wherein the second therapeutic agent and/or DNase is administered to the patient before, at the same time as, or after the unfractionated heparin or physiologically acceptable salt thereof or derivative thereof.

19. The method of claim 1, wherein the reservoir has a liquid medicament inlet port and a medicament outlet port, and/or the vibrating mesh nebuliser further comprises:
 an aerosol generator comprising a vibratable membrane having a plurality of apertures extending between a first surface and a second surface thereof, wherein the aerosol generator aerosolises at least a portion of the medicament into an aerosol;
 a gas venting inlet to permit a gas to enter the vibrating mesh nebuliser and form a mixture with the aerosol;
 a passage through which the mixture of the aerosol and the gas is delivered to an outlet port of the vibrating mesh nebuliser; or
 a combination thereof.

20. The method of claim 15, wherein:
(a) the second therapeutic agent is selected from the group consisting of a bronchodilator, a mucolytic, a mucokinetic, an anti-inflammatory, a protease inhibitor, $\alpha 1$-antitrypsin, a mucoregulator, an anti-pathogenic agent, a gene therapy vector, an antioxidant, a steroid, a corticosteroid, and a combination thereof; or
(b) the DNase is a type I DNase, or a human type I DNase, or the DNase is a recombinant DNase.

* * * * *